United States Patent [19]

Jacobsen et al.

[11] Patent Number: 5,847,148

[45] Date of Patent: Dec. 8, 1998

[54] THIADIAZOLE DERIVATIVES USEFUL FOR THE TREATMENT OF DISEASES RELATED TO CONNECTIVE TISSUE DEGRADATION

[75] Inventors: Eric J. Jacobsen, Plainwell; Mark A. Mitchell, Kalamazoo; Heinrich J. Schostarez, Portage; Donald E. Harper, Plainwell, all of Mich.

[73] Assignee: Pharmacia & Upjohn Company, Kalamazoo, Mich.

[21] Appl. No.: 835,599

[22] Filed: Apr. 10, 1997

[51] Int. Cl.$^6$ ............... C07D 285/125; C07D 209/08; C07D 241/04; A01N 43/82

[52] U.S. Cl. ............ 548/140; 514/363; 548/491; 548/579; 546/334; 544/358; 544/360; 544/106; 544/60; 549/436

[58] Field of Search ............... 548/140, 491, 548/579; 514/363; 544/358, 360, 106, 60; 549/436; 546/334

[56] References Cited

FOREIGN PATENT DOCUMENTS

| | | | |
|---|---|---|---|
| 0574758A | 12/1993 | European Pat. Off. ...... | C07D 209/48 |
| 62-220954 | 9/1987 | Japan . | |
| 2282598 | 12/1995 | United Kingdom ......... | C07C 234/82 |
| 92 09563 | 6/1992 | WIPO ........................ | C07C 259/00 |
| 93/21942 | 11/1993 | WIPO ........................ | A61K 37/02 |
| 95/04033-A1 | 2/1995 | WIPO ........................ | C07C 259/06 |
| 95 19956 A | 7/1995 | WIPO ........................ | C07C 259/06 |
| 96 40745 A | 12/1996 | WIPO ........................ | C07K 5/062 |
| 96/40745 | 12/1996 | WIPO ........................ | C07K 5/062 |
| 95/09841 | 4/1997 | WIPO ........................ | C07C 323/60 |

*Primary Examiner*—Johann Richter
*Assistant Examiner*—Dominic Keating
*Attorney, Agent, or Firm*—Lucy X. Yang

[57] ABSTRACT

The present invention provides novel thiadiazole derivatives represented by formula I:

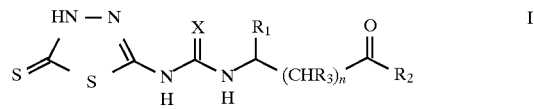

or pharmaceutical acceptable salts thereof wherein the compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation.

15 Claims, No Drawings

THIADIAZOLE DERIVATIVES USEFUL FOR THE TREATMENT OF DISEASES RELATED TO CONNECTIVE TISSUE DEGRADATION

CROSS-REFERENCE TO RELATED APPLICATION

This application claims the benefit of the following provisional application. U.S. Ser. No. 60/016,003, filed Apr. 23, 1996, under 35 USC 119(e)(i).

FIELD OF THE INVENTION

The present invention relates to novel thiadiazole derivatives or pharmaceutically acceptable salts thereof, and pharmaceutical compositions containing them. Particularly, the present invention relates to the compounds having a thiadiazole heterocycle and a urea or a thiocarbonyl side chain which are useful in the treatment of diseases related to connective tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463, (1992); Emonard, H. et al., Cellular and molecular Biology, Vol. 36, pp 131–153, (1990); Docherty, A. J. P. et al., Annals of the Rheumatic, Vol. 49, pp 469–479, (1990)).

The compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation, and other diseases related to connective tissue degradation.

INFORMATION DISCLOSURE

Peptide MMP inhibitors are described in the following:

International Publication No. WO 95/09841 discloses new hydroxamic acid derivatives of amino acid amide compounds useful as TNF release and matrix metalloprotease inhibitors, e.g., for treating inflammation, fever or arthritis.

International Publication No. WO 95/04033-A1 discloses new succinamide derivatives useful as gelatinase and collagenase inhibitors.

International Publication No. WO 93/21942 discloses matrix metallo protease inhibitors for promoting tumour regression by inhibiting cancer cell proliferation and angiogenesis, atherosclerosis, ovarian carcinoma, melanoma and sarcoma.

European Patent Publication 0,574,758A discloses new hydroxamic acid derivatives useful as collagenase inhibitors for the treatment of arthritis, tumors, atherosclerosis, etc.

UK Patent Application GB 2,282,598A discloses hydroxysuccinyl hydroxyamines useful in the prophylaxis or treatment of diseases or conditions mediated by metalloproteinases and/or tumour necrosis factor.

Compounds in these references bear no structural resemblance to the thiadiazole MMP inhibitors described in the present invention.

Compounds having thiadiazole structure have been reported in number of publications and patents. For example, chemical abstract discloses N-(4,5-dihydro-5-thioxo-1,3,4-thiadiazol-2-yl)-N'-(5,6,7,8 tetrahydro-1-naphthalenyl)-urea (RN 144331-80-6) and 3-[[[4,5-dihydro-5-thioxo-1,3,4-thiadiazol-2-yl)amino]carbonyl]amino] propanamide (RN 114520-21-7); International Publication No. WO96/40745 discloses. However, chemical structure of these publications do not overlap with the compounds of the present invention.

SUMMARY OF THE INVENTION

The present invention provides novel thiadiazole derivatives represented by formula I

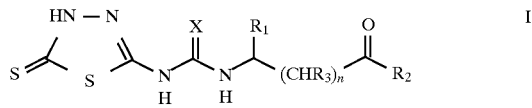

or pharmaceutical acceptable salts thereof wherein:

$X$ is
  a) O, or
  b) S;

$R_1$ is
  a) H,
  b) $C_{1-6}$ alkyl,
  c) —$(CH_2)_i$-aryl,
  d) —$(CH_2)_j$-cycloalkyl,
  e) —$(C_{1-4}$ alkyl)—O—$R_4$,
  f) —$(C_{1-4}$ alkyl)—S—$R_4$,
  f) —$(CH_2)_j$-Het,
  g) —C(=O)—O—$R_4$,
  h) —C(=O)—$NR_5R_5$, or
  i) —$(CH_2)_j$—O—$Si(R_4)_3$;

$R_2$ is
  a) —O—$R_5$, or
  b) —$NR_6 R_7$;

$R_3$ is
  a) H,
  b) $C_{1-6}$ alkyl,
  c) —$(CH_2)_i$-aryl,
  d) —$(CH_2)_j$-cycloalkyl,
  e) —$(C_{1-4}$ alkyl)—O—$R_4$,
  f) —$(C_{1-4}$ alkyl)—S—$R_4$, or
  g) —$OR_4$;

$R_4$ is
  a) H,
  b) $C_{1-6}$ alkyl, or
  c) —$(CH_2)_i$-aryl, $R_5$ is
  a) H,
  b) $C_{1-6}$ alkyl, or
  c) aryl;

$R_6$ and $R_7$ may be the same or differently
  a) H,
  b) $C_{1-6}$ alkyl,
  c) $C_{1-6}$ $OR_4$,
  d) —$(CH_2)_i$-aryl, e) —(CH$_2$)$_j$-cycloalkyl,
f) —(CH$_2$)$_j$-Het,
g) —(CH$_2$)—Q,
h) —(CH$_2$)$_j$—C(=O)—OR$_4$,
i) —(CH$_2$)$_j$—C(=O)—NR$_5$R$_5$,
j) 5-(((5-(dimethylamino)-1-naphthalenyl)sulfonyl) amino)pentyl, or R$_6$ and R$_7$ taken together with the linking N-atom to form
k) azetidinyl,
l) pyrrolidinyl,
m) piperidinyl,
n) morpholino,
o) 4-thiomorpholinyl, or p) 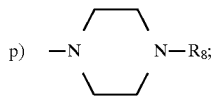

R$_8$ is
a) H,
b) C$_{1-6}$ alkyl,
c) —(CH$_2$)$_i$-aryl,
d) benzhydryl, or
e) —(CH$_2$)$_i$-Het;

aryl is
phenyl, biphenyl, or naphthalene, optionally substituted with one to five of the following:
a) C$_{1-4}$ alkyl,
b) —OR$_4$,
c) halogen,
d) —NR$_5$R$_5$,
e) —C(=O)—NR$_5$R$_5$,
f) —NHC(=O)R$_4$,
g) —SO$_2$NR$_5$R$_5$,
h) —NHSO$_2$R$_5$,
i) —NO$_2$,
j) —CF$_3$, or
k) —O—Si(R$_4$)$_3$;

Het is
a 5-, 6-, 9-, or 10-membered heteroaromatic moiety having one or more atoms selected from the group consisting of N, O, and S;

Q is
a saturated 5-, or 6-membered heterocyclic moiety having 1–2 atoms selected from the group consisting of N, O, and S;

i is 0, 1, 2, 3, or 4; j is 1, 2, 3, or 4; n is 0, or 1; and with the proviso that when R$_1$ is isobutyl R$_6$ and R$_7$ are other than methyl.

The invention also includes compounds of formula III

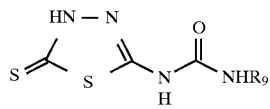

wherein
R$_9$ is benzyl, or 2-phenylethyl.

The present invention provides novel thiadiazole derivatives useful as preventatives and therapeutics for diseases related to connective tissue degradation.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix C$_{i-j}$ defines the number of carbon atoms present from the integer "i" to the integer "j" inclusive. Thus, C$_{4-1}$ alkyl refers to alkyl of 1–4 carbon atoms, inclusive, or methyl, ethyl, propyl, butyl and isomeric forms thereof.

The term "C$_{4-1}$ alkyl" and "C$_{6-1}$ alkyl" refer to alkyl groups having one to four or one to six carbon atoms respectively such as, for example, methyl, ethyl, n-propyl, n-butyl, n-pentyl, n-hexyl and isomeric forms thereof, and preferably an alkyl group having 1 to 4 carbon atoms.

The C$_{6-1}$ alkyl group may optionally be substituted by one or more substituents selected from the group consisting of a halogen atom, a hydroxy group, or —CN group such as, for example, fluoromethyl, difluoromethyl, fluoroethyl, cyanomethyl and the like.

The term "cycloalkyl" refers to three to six carbon atoms forming cyclopropyl, cyclobutyl, cyclopentyl, cyclohexyl and isomeric forms thereof, and preferably an cycloalkyl group having 5 to 6 carbon atoms.

The term "halogen" refers to fluoro, chloro, bromo, or iodo, preferably fluoro.

The term "Het" refers to a 6-, 9- or 10-membered heteroaromatic moiety having one or more atoms selected form the group consisting of nitrogen, oxygen, and sulfur forming such groups as, for example, pyridyl, pyrimidinyl, pyridazinyl, indolyl, isoindolyl, 2-benzimidazole, piperonyl, indazolyl, or quinolyl.

The term "Q" refers to a saturated 5-, or 6-membered heterocyclic moiety having 1–2 atoms selected from the group consisting of nitrogen, oxygen, and sulfur forming such groups as, for example, dioxolane, imidazolidine, dithiolane, oxathiolane, oxazolidine, pyrrolidinyl, piperidinyl, piperazinyl, morpholino or thiomorpholino.

Within the definition of the terms "Het", and "Q", the nitrogen atom forming the hetero rings may have a protective group such as an acetyl or hydroxyacetyl group.

The compounds of the present invention can be converted to their salts according to conventional methods.

The term "pharmaceutically acceptable salts" refers to salts useful for administering the compounds of this invention and these include hydrochloride, hydrobromide, hydroiodide, trifluoroacetic acid, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

Certain of the thiadiazole derivatives of the present invention are preferred.

The preferred R$_1$ substituent is phenyl, benzyl, 4-tert-butylphenylmethyl, 4-bromophenylmethyl, 4-fluorophenylmethyl, 4-methoxyphenylmethyl, 4-nitrophenylmethyl, 4-hydroxyphenylmethyl, 4-aminophenylmethyl, 2,3,4,5,6,-pentafluorophenylmethyl, cyclohexylmethyl, benzyloxymethyl, 1-benzyloxyethyl, 2-indolylmethyl, benzylthiomethyl, 4-methylbenzylthiomethyl, 4-35 methyloxybenzylthiomethyl, tert-butyloxymethyl, 1-tert-butyloxyethyl, biphenylmethyl, and isobutyl.

The preferred R$_2$ substituent is —NR$_6$R$_7$, R$_6$ and R$_7$ may be the same or different. The preferred R$_6$ and R$_7$ substituents are hydrogen, methyl, isopropyl, n-butyl, cyclohexylmethyl, 3-hydroxypropyl, benzyl, 3,4-dimethoxyphenylmethyl, 2-phenylethyl, 4-trifluoromethylphenylmethyl, 4-nitrophenylmethyl, 4-ter-tbutylphenylmethyl, 3-phenylpropyl, 4-phenylbutyl, 2-pyridylmethyl, 3-pyridylmethyl, 4-pyridylmethyl, 2-benzimidazolemethyl, 1-naphthylmethyl, 2-morpholinoethyl, piperonylmethyl, N-methyl-β-alaninamide, β-alanine or $R_6$ and $R_7$ taken together with the linking N-atom forming morpholino, pyrrolidinyl, piperidinyl, 4-thiomorpholinyl, 4-phenylpiperazinyl, 4-benzylpiperazinyl, 4-(4-methoxyphenyl)piperazinyl, 4-(2-pyrimidinyl)piperazinyl, 4-(2-pyridyl)piperazinyl, and 4-benzhydryl.

The preferred structure and absolute configurations of the compounds claimed in the present invention are as represented in the structure II, which are the optically pure enantiomers having the (S)-configuration according the Cahn-Ingold-Prelog nomenclature system at C2 of propanamide. The (R)-configuration enantiomers are useful in the same manner as the (S)-enantiomer. The racemic mixtures are useful in the same way and for the same purpose as the (S) or (R) enantiomers; the difference is that more racemic material may be used to produce the same inhibitory effect. Enantiomerically pure compounds can be prepared directly by using the corresponding enantiomerically pure starting material as illustrated in Scheme I and Examples.

Depending on substituents, the compounds of this invention may exist in geometric, optical and other isomeric forms and this invention embraces any of these isomers or enantiomers.

Particularly preferred compounds of this invention are as follows:

(1) N-[[(4,5-Dihydro-5-thioxo-1,3,4-thiadiazol-2-yl)amino]carbonyl]-L-phenylalanine methyl ester,
(2) α-[[[(4,5-Dihydro-5-thioxo-1,3,4-thiadiazol-2-yl)amino]carbonyl]amino]-N-methyl-(S)-benzenepropanamide,
(3) N-[[(4,5-Dihydro-5-thioxo-1,3,4-thiadiazol-2-yl)amino]carbonyl]-D-phenylalanine methyl ester,
(4) α-[[[(4,5-Dihydro-5-thioxo-1,3,4-thiadiazol-2-yl)amino]carbonyl]amino]-N-methyl-(R)-benzenepropanamide,
(5) α-[[[(4,5-Dihydro-5-thioxo-1,3,4-thiadiazol-2-yl)amino]carbonyl]amino]-N-(phenylmethyl)-(S)-benzenepropanamide,
(6) α-[[[(4,5-Dihydro-5-thioxo-1,3,4-thiadiazol-2-yl)amino]carbonyl]amino]-N-(phenylethyl)-(S)-benzenepropanamide,
(7) α-[[[(4,5-Dihydro-5-thioxo-1,3,4-thiadiazol-2-yl)amino]carbonyl]amino]-N-(2-pyridinylmethyl)-(S)-benzenepropanamide,
(8) α-[[[(4,5-Dihydro-5-thioxo-1,3,4-thiadiazol-2-yl)amino]carbonyl]amino]-N,N-dimethyl-(S)-benzenepropanamide,
(9) α-[[[(4,5-Dihydro-5-thioxo-1,3,4-thiadiazol-2-yl)amino]carbonyl]amino]-(S)-benzenepropanamide,
(10) α-[[[(4,5-Dihydro-5-thioxo-1,3,4-thiadiazol-2-yl)amino]carbonyl]amino]-N-(1-methylethyl)-(S)-benzenepropanamide,
(11) N-Butyl-α-[[[(4,5-dihydro-5-thioxo-1,3,4-thiadiazol-2-yl)amino]carbonyl]amino]-(S)-benzenepropanamide,
(12) N-[[(4,5-Dihydro-5-thioxo-1,3,4-thiadiazol-2-yl)amino]carbonyl]-L-phenylalanine,
(13) α-[[[(4,5-Dihydro-5-thioxo-1,3,4-thiadiazol-2-yl)amino]carbonyl]amino]-N-methyl-(S)-1H-indole-3-propanamide,
(14) (S)-1-[2-[[[(4,5-Dihydro-5-thioxo-1,3,4-thiadiazol-2-yl)amino]carbonyl]amino]-1-oxo-3-phenylpropyl]-4-(phenylmethyl)piperazine,
(15) (S)-1-[2-[[[(4,5-Dihydro-5-thioxo-1,3,4-thiadiazol-2-yl)amino]carbonyl]amino]-1-oxo-3-phenylpropyl]-4-(2-pyridinyl)piperazine,
(16) α-[[[(4,5-Dihydro-5-thioxo-1,3,4-thiadiazol-2-yl)amino]carbonyl]amino]-N-[(3,4-dimethoxyphenyl)methyl]-(S)-benzenepropanamide,
(17) α-[[[(4,5-Dihydro-5-thioxo-1,3,4-thiadiazol-2-yl)amino]carbonyl]amino]-N-(4-pyridinylmethyl)-(S)-benzenepropanamide,
(18) α-[[[(4,5-Dihydro-5-thioxo-1,3,4-thiadiazol-2-yl)amino]carbonyl]amino]-N-(3-5 pyridinylmethyl)-(S)-benzenepropanamide,
(19) α-[[[(4,5-Dihydro-5-thioxo-1,3,4-thiadiazol-2-yl)amino]carbonyl]amino]-N-[2-(4-morpholinyl)ethyl]-(S)-benzenepropanamide,
(20) α-[[[(4,5-Dihydro-5-thioxo-1,3,4-thiadiazol-2-yl)amino]carbonyl]amino]-N-methyl-4-bromobenzenepropanamide,
(21) (S)-1-[2-[[[(4,5-Dihydro-5-thioxo-1,3,4-thiadiazol-2-yl)amino]carbonyl]amino]-1-oxo-3-phenylpropyl]-4-(4-methoxyphenyl)piperazine,
(22) (S)-1-[2-[[[(4,5-Dihydro-5-thioxo-1,3,4-thiadiazol-2-yl)amino]carbonyl]amino]-1-oxo-3-phenylpropyl]-4-(2-pyrimidinyl)piperazine,
(23) (S)-1-[2-[[[(4,5-Dihydro-5-thioxo-1,3,4-thiadiazol-2-yl)amino]carbonyl]amino]-1-oxo-3-(pentafluorophenyl)propyl]-4-(2-pyridinyl)piperazine,
(24) (S)-N-[[(4,5-Dihydro-5-thioxo-1,3,4-thiadiazol-2-yl)amino]carbonyl]-2-phenylglycine methyl ester,
(25) α-[[[(4,5-Dihydro-5-thioxo-1,3,4-thiadiazol-2-yl)amino]carbonyl]amino]-N-methyl-(S)-benzeneacetamide,
(26) α-[[[(4,5-Dihydro-5-thioxo-1,3,4-thiadiazol-2-yl)amino]carbonyl]amino]-4-fluoro-N-methyl-(S)-benzenepropanamide,
(27) (S)-1-[2-[[[(4,5-Dihydro-5-thioxo-1,3,4-thiadiazol-2-yl)amino]carbonyl]amino]-1-oxo-3-(4-fluorophenyl)propyl]-4-(2-pyridinyl)piperazine,
(28) 2-[[[(4,5-Dihydro-5-thioxo-1,3,4-thiadiazol-2-yl)amino]carbonyl]amino]-4-methyl-N-(2-phenylethyl)-(S)-pentanamide,
(29) 2-[[[(4,5-Dihydro-5-thioxo-1,3,4-thiadiazol-2-yl)amino]carbonyl]amino]-4-methyl-N-(phenylmethyl)-(S)-pentanamide,
(30) N-[[(4,5-Dihydro-5-thioxo-1,3,4-thiadiazol-2-yl)amino]carbonyl]-O-methyl-L-tyrosine methyl ester,
(31) α-[[[(4,5-Dihydro-5-thioxo-1,3,4-thiadiazol-2-yl)amino]carbonyl]amino]-4-methoxy-N-methyl-(S)-benzenepropanamide,
(32) N-[[(4,5-Dihydro-5-thioxo-1,3,4-thiadiazol-2-yl)amino]carbonyl]-L-(4-nitrophenyl)alanine methyl ester,
(33) α-[[[(4,5-Dihydro-5-thioxo-1,3,4-thiadiazol-2-yl)amino]carbonyl]amino]-N-methyl-4-nitro-(S)-benzenepropanamide,
(34) α-[[[(4,5-Dihydro-5-thioxo-1,3,4-thiadiazol-2-yl)amino]carbonyl]amino]-4-nitro-N-(2-phenylethyl)-(S)-benzenepropanamide,
(35) N-Butyl-α-[[[(4,5-dihydro-5-thioxo-1,3,4-thiadiazol-2-yl)amino]carbonyl]amino]-4-nitro-(S)-benzenepropanamide,
(36) (S)-4-[2-[[[(4,5-Dihydro-5-thioxo-1,3,4-thiadiazol-2-yl)amino]carbonyl]amino]-1-oxo-3-phenylpropyl]morpholine,
(37) α-[[[(4,5-Dihydro-5-thioxo-1,3,4-thiadiazol-2-yl)amino]carbonyl]amino]-N-(4-phenylbutyl)-(S)-benzenepropanamide,
(38) N-Cyclohexylmethyl-α-[[[(4,5-Dihydro-5-thioxo-1,3,4-thiadiazol-2-yl)amino]carbonyl]amino]-(S)-benzenepropanamide,

(39) (S)-4-[2-[[[(4,5-Dihydro-5-thioxo-1,3,4-thiadiazol-2-yl)amino]carbonyl]amino]-1-oxo-3-phenylpropyl]pyrrolidine,

(40) (S)-4-[2-[[[(4,5-Dihydro-5-thioxo-1,3,4-thiadiazol-2-yl)amino]carbonyl]amino]-1-oxo-3-phenylpropyl]thiomorpholine,

(41) α-[[[(4,5-Dihydro-5-thioxo-1,3,4-thiadiazol-2-yl)amino]carbonyl]amino]-N-(3-hydroxypropyl)-(S)-benzenepropanamide,

(42) N-[[[(4,5-Dihydro-5-thioxo-1,3,4-thiadiazol-2-yl)amino]carbonyl]-L-phenylalanyl-β-alanine ethyl ester,

(43) N-[[(4,5-Dihydro-5-thioxo-1,3,4-thiadiazol-2-yl)amino]carbonyl]-L-phenylalanyl-N-methyl-β-alaninamide,

(44) N-[[[(4,5-Dihydro-5-thioxo-1,3,4-thiadiazol-2-yl)amino]carbonyl]-L-phenylalanyl-β-alanine,

(45) N-[[(4,5-Dihydro-5-thioxo-1,3,4-thiadiazol-2-yl)amino]carbonyl]-O-[(1,1-dimethylethyl)dimethylsilyl]-L-serine methyl ester,

(46) 2-[[[(4,5-Dihydro-5-thioxo-1,3,4-thiadiazol-2-yl)amino]carbonyl]amino]-3-[(1,1-dimethylethyl)dimethylsilyloxy]-N-methyl-(S)-propanamide,

(47) N-[[(4,5-Dihydro-5-thioxo-1,3,4-thiadiazol-2-yl)amino]carbonyl]-O-[(1,1-dimethylethyl)dimethylsilyl]-L-tyrosine methyl ester,

(48) α-[[[(4,5-Dihydro-5-thioxo-1,3,4-thiadiazol-2-yl)amino]carbonyl]amino]-4-hydroxy-N-methyl-(S)-benzenepropanamide,

(49) α-[[[(4,5-Dihydro-5-thioxo-1,3,4-thiadiazol-2-yl)amino]carbonyl]amino]-N-(piperonyl)-(S)-benzenepropanamide,

(50) (S)-1-[2-[[[(4,5-Dihydro-5-thioxo-1,3,4-thiadiazol-2-yl)amino]carbonyl]amino-]-1-oxo-3-phenylpropyl]-4-phenylpiperazine,

(51) α-[[[(4,5-Dihydro-5-thioxo-1,3,4-thiadiazol-2-yl)amino]carbonyl]amino]-N-(3-phenylpropyl)-(S)-benzenepropanamide,

(52) α-[[[(4,5-Dihydro-5-thioxo-1,3,4-thiadiazol-2-yl)amino]carbonyl]amino]-N-[(4-35 trifluoromethylphenyl)methyl]-(S)-benzenepropanamide,

(53) α-[[[(4,5-Dihydro-5-thioxo-1,3,4-thiadiazol-2-yl)amino]carbonyl]amino]-N-[(4-nitrophenyl)methyl]-(S)-benzenepropanamide,

(54) α-[[[(4,5-Dihydro-5-thioxo-1,3,4-thiadiazol-2-yl)amino]carbonyl]amino]-N-[[4-(1,1-dimethylethyl)phenyl]methyl]-(S)-benzenepropanamide,

(55) (S)-1-[2-[[[(4,5-Dihydro-5-thioxo-1,3,4-thiadiazol-2-yl)amino]carbonyl]amino]-1-oxo-3-phenylpropyl]-4-(benzhydryl)piperazine,

(56) (S)-1-[2-[[[(4,5-Dihydro-5-thioxo-1,3,4-thiadiazol-2-yl)amino]carbonyl]amino]-1-oxo-3-phenylpropyl]piperazine trifluoroacetic acid,

(57) N-(1H-Benzimidazol-2-ylmethyl)-α-[[[(4,5-dihydro-5-thioxo-1,3,4-thiadiazol-2-yl)amino]carbonyl]amino]-(S)-benzenepropanamide,

(58) α-[[[(4,5-Dihydro-5-thioxo-1,3,4-thiadiazol-2-yl)amino]carbonyl]amino]-N-(1-naphthylmethyl)-(S)-benzenepropanamide,

(59) N-[[(4,5-Dihydro-5-thioxo-1,3,4-thiadiazol-2-yl)amino]carbonyl]-L-(4-20 aminophenyl)alanine methyl ester,

(60) α-[[[(4,5-Dihydro-5-thioxo-1,3,4-thiadiazol-2-yl)amino]carbonyl]amino]-N-methyl-(S)-cyclohexanepropanamide,

(61) α-[[[(4,5-Dihydro-5-thioxo-1,3,4-thiadiazol-2-yl)amino]carbonyl]amino]-N-(phenylmethyl)-(S)-cyclohexanepropanamide,

(62) α-[[[(4,5-Dihydro-5-thioxo-1,3,4-thiadiazol-2-yl)amino]carbonyl]amino]-N-(2-phenylethyl)-(S)-cyclohexanepropanamide,

(63) N-[[(4,5-Dihydro-5-thioxo-1,3,4-thiadiazol-2-yl)amino]carbonyl]-O-(phenylmethyl)-L-serine methyl ester,

(64) N-[[(4,5-Dihydro-5-thioxo-1,3,4-thiadiazol-2-yl)amino]carbonyl]-O-(phenylmethyl)-L-threonine methyl ester,

(65) N-[[(4,5-Dihydro-5-thioxo-1,3,4-thiadiazol-2-yl)amino]carbonyl]-S-[(4-methylphenyl)methyl]-L-cysteine methyl ester,

(66) 2-[[[(4,5-Dihydro-5-thioxo-1,3,4-thiadiazol-2-yl)amino]carbonyl]amino]-N-methyl-3-(phenylmethoxy)-(2S)-butanamide,

(67) N-[[(4,5-Dihydro-5-thioxo-1,3,4-thiadiazol-2-yl)amino]carbonyl]-O-(1,1-dimethylethoxy)-L-serine methyl ester,

(68) N-[[(4,5-Dihydro-5-thioxo-1,3,4-thiadiazol-2-yl)amino]carbonyl]-S-[(4-methoxyphenyl)methyl]-L-cysteine methyl ester,

(69) 2-[[[(4,5-Dihydro-5-thioxo-1,3,4-thiadiazol-2-yl)amino]carbonyl]amino]-N-methyl-3-phenylmethoxy-(S)-propanamide,

(70) 2-[[[(4,5-Dihydro-5-thioxo-1,3,4-thiadiazol-2-yl)amino]carbonyl]amino]-N-methyl-3-[[(4-methylphenyl)methyl]thio]-(R)-propanamide,

(71) N-[[(4,5-Dihydro-5-thioxo-1,3,4-thiadiazol-2-yl)amino]carbonyl]-S-(phenylmethyl)-L-cysteine methyl ester,

(72) 2-[[[(4,5-Dihydro-5-thioxo-1,3,4-thiadiazol-2-yl)amino]carbonyl]amino]-N-methyl-3-[(phenylmethyl)thio]-(R)-propanamide,

(73) 2-[[[(4,5-Dihydro-5-thioxo-1,3,4-thiadiazol-2-yl)amino]carbonyl]amino]-3-(1,1-dimethylethoxy)-N-methyl-(S)-propanamide,

(74) N-[[(4,5-Dihydro-5-thioxo-1,3,4-thiadiazol-2-yl)amino]carbonyl]-O-(1,1-dimethylethoxy)-L-threonine methyl ester,

(75) 2-[[[(4,5-Dihydro-5-thioxo-1,3,4-thiadiazol-2-yl)amino]carbonyl]amino]-3-(1,1-dimethylethoxy)-N-methyl-(S)-butanamide,

(76) α-[[[(4,5-Dihydro-5-thioxo-1,3,4-thiadiazol-2-yl)-amino]carbonyl]amino]-N-[5-[[[5-(dimethylamino)-1-naphthalenyl]sulfonyl]amino]pentyl]-(S)-benzenepropanamide,

(77) α-[[[(4,5-Dihydro-5-thioxo-1,3,4-thiadiazol-2-yl)amino]carbonyl]amino]-N-methyl-(2,3,4,5,6-pentafluorobenzene)-(S)-benzene-propanamide,

(78) α-[[[(4,5-Dihydro-5-thioxo-1,3,4-thiadiazol-2-yl)amino]carbonyl]amino]-(S)-(1,1'-biphenyl)-4-propanoic acid methyl ester,

(79) α-[[[(4,5-Dihydro-5-thioxo-1,3,4-thiadiazol-2-yl)amino]carbonyl]amino]-N-methyl-(S)-(1,1'-biphenyl)-4-propanamide,

(80) N-[[(4,5-Dihydro-5-thioxo-1,3,4-thiadiazol-2-yl)amino]carbonyl]-4-(1,1-dimethylethyl)-L-phenylalanine methyl ester,

(81) α-[[[(4,5-Dihydro-5-thioxo-1,3,4-thiadiazol-2-yl)amino]carbonyl]amino]-4-(1,1-dimethylethyl)-N-methyl-(S)-benzenepropanamide,

(82) N-[[(4,5-Dihydro-5-thioxo-1,3,4-thiadiazol-2-yl)amino]thioxomethyl]-L-phenylalanine methyl ester,

(83) α-[[[(4,5-Dihydro-5-thioxo-1,3,4-thiadiazol-2-yl)-amino]thioxomethyl]amino]-N-methyl-(S)-benzenepropanamide,

(84) β-[[[(4,5-Dihydro-5-thioxo-1,3,4-thiadiazol-2-yl)amino]carbonyl]amino]-benzenebutanoic acid ethyl ester,

(85) α-[[[[(4,5-Dihydro-5-thioxo-1,3,4-thiadiazol-2-yl)-amino]carbonyl]amino]methyl]-N-methylbenzenepropanamide,

(86) β-[[[[(4,5-Dihydro-5-thioxo-1,3,4-thiadiazol-2-yl)-amino]carbonyl]amino]methyl]-N-methylbenzenepropanamide,

(87) N-(4,5-Dihydro-5-thioxo-1,3,4-thiadiazol-2-yl)-N'-2-phenylethyl-urea, or

(88) N-(4,5-Dihydro-5-thioxo-1,3,4-thiadiazol-2-yl)-N'-phenylmethyl-urea.

The compounds represented by the general formula I can be prepared by reactions outlined in Scheme I. For simplicity, only a single enantiomerically pure compound is presented. The procedure can be carried out for both the racemate or a single enantiomer. In Scheme I, compound 3, the isocyanate (wherein X is O) or the isothio cyanate (wherein X is S) of the desired amino acids is either commercially available or can be prepared by treating an appropriate amino acid ester 2 with phosgene or thiophosgene following the procedures described in *J. Org. Chem.*, Vol. 57, pp 7364–7365 (1992); *J. Chem. Res. Miniprint*, Vol 2, pp 201–213 (1993); *J. Am. Chem. Soc.*, Vol. 40, p 642 (1918). A wide choice of ester 2 can be obtained directly from corresponding commercially available amino acid 1 or be prepared by procedures known in the art. The following publications further describe and exemplify these procedures: *J. Am. Chem. Soc.*, Vol. 77, pp 1–6 (1955); *Tetrahedron Lett.*, Vol. 34, pp 47–50 (1993); *J. Chem. Soc.Chem. Commun.*, pp 1153–1155 (1993); *J. Org. Chem.*, Vol. 26, pp 4062–4065 (1961); *J. Org. Chem.*, Vol. 56, pp 2553–2557 (1991); *Tetrahedron Lett.*, Vol. 34, pp 7557–7560 (1993). For purposes of this reaction, the amino acid 1 may, if desired, be protected by a group which renders the amino group substantially inert to the reaction conditions. The protecting groups generally utilized in the present invention are either a tert-butyl carbamate (BOC) group or a benzyl carbamate (Cbz) group, which are removed with either trifluoroacetic acid (TFA) or ammonium formate-Pd/C, respectively. The reaction of isocyanate 3 with thiadiazole 4 in a suitable solvent such as tetrahydrofuran (THF) at a suitable temperature in the range −10° C. to 30° C. affords the desired thiadiazole analog 5. Treatment of ester analogs 5 with the desired amine (neat or diluted in ethanol) at room temperature provides amide 6.

In a similar fashion as described above, compounds represented by formula III can be prepared as outlined in Scheme II. The reaction of amino thiadiazole 4 with isocyanate 7 (commercially available) provides structure 8.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase, the compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or collagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% NaN$_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 $\mu$M against stromelysin will display therapeutic effects in connective tissue disorders.

TABLE 1

MMP Inhibition Constants (Ki, $\mu$M) for Thiadiazole Derivatives

| Example No. | Stromelysin Ki ($\mu$M) | Example No. | Stromelysin Ki ($\mu$M) |
|---|---|---|---|
| 1 | 0.9 | 2 | 0.27 |
| 3 | 2.2 | 4 | 5 |
| 5 | 0.52 | 6 | 0.3 |
| 7 | 1.1 | 8 | 0.25 |
| 9 | 3.3 | 10 | 1.4 |
| 11 | — | 12 | 3.1 |
| 13 | 2.5 | 14 | 0.86 |
| 15 | 0.52 | 16 | 0.49 |
| 17 | 1.27 | 18 | 2.01 |
| 19 | 1.99 | 20 | 0.80 |
| 21 | 1.01 | 22 | 0.42 |
| 23 | 0.01 | 24 | 7.66 |
| 25 | 4.13 | 26 | 0.1 |
| 27 | 0.27 | 28 | 3.49 |
| 29 | 4.42 | 30 | 2.75 |
| 31 | 0.46 | 32 | 1.87 |
| 33 | 0.33 | 34 | 0.21 |
| 35 | 0.35 | 36 | 0.92 |
| 37 | 0.82 | 38 | 0.81 |
| 39 | 0.65 | 40 | 0.38 |
| 41 | 1.12 | 42 | 0.78 |
| 43 | 1.34 | 44 | 1.08 |
| 45 | 1.53 | 46 | 0.75 |
| 47 | 6.37 | 48 | 0.40 |
| 49 | 1 | 50 | 1.68 |
| 51 | 1.02 | 52 | 0.75 |
| 53 | 1.31 | 54 | 1.74 |
| 55 | 4.25 | 56 | 5.27 |
| 57 | 0.64 | 58 | 0.80 |
| 59 | 2.95 | 60 | — |
| 61 | — | 62 | 0.65 |
| 63 | 2.39 | 64 | 9.56 |
| 65 | 2.55 | 66 | 0.76 |
| 67 | 6.7 | 68 | 2.05 |
| 69 | 2.03 | 70 | 1.2 |
| 71 | 2.51 | 72 | 1.05 |
| 73 | 1.6 | 74 | 1.87 |

TABLE 1-continued

MMP Inhibition Constants (Ki, $\mu$M) for Thiadiazole Derivatives

| Example No. | Stromelysin Ki ($\mu$M) | Example No. | Stromelysin Ki ($\mu$M) |
|---|---|---|---|
| 75 | 0.67 | 76 | — |
| 77 | 0.02 | 78 | 3.02 |
| 79 | 7.39 | 80 | 0.80 |
| 81 | 1.82 | — | — |

In order to more fully illustrate the nature of the invention and the manner of practicing the same, the following experimental examples are presented, but they should not be taken as limiting.

EXAMPLE 1

Preparation of N-[[(4,5-Dihydro-5-thioxo-1,3,4-thiadiazol-2-yl)amino]carbonyl]-L-phenylalanine methyl ester.

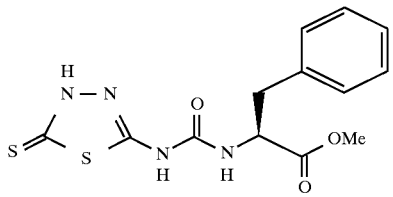

The isocyanate of L-phenylalanine methyl ester is synthesized following the general procedure of Nowick, *J. Am. Chem. Soc.*, Vol. 77, pp. 1–6 (1955). Phosgene (7.90 mL, 15.2 mmol, 1.93M in toluene) is added to a mixture of L-phenylalanine methyl ester hydrochloride (2.57 g, 11.9 mmol), pyridine (3.90 ml, 48.2 mmol), and CH$_2$Cl$_2$ (40 ml) at 0° C. The mixture is stirred for 2 hours at 0° C. and then diluted with EtOAc (150 mL). The organic layer is washed with cold 5% HCl (2×40 mL) and cold brine (50 mL). The organic layers are dried (MgSO$_4$), filtered, and concentrated to give 2.5 g of the isocyanate as an oil which is carried on crude.

A solution of the residue (11.9 mmol) and THF (35.0 mL) is cooled to 0° C. To this is added 5-amino-1,3,4-thiadiazole-2-thiol (1.60 g, 12.0 mmol) and the solution stirred at 0° C. for 1 hour and at room temperature for 16 hours. Aqueous workup (EtOAc, MgSO$_4$) and purification by flash chromatography (0→5% MeOH/CH$_2$Cl$_2$) gives 2.35 g (58%) of the title compound.

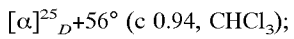

IR (mineral oil) 3195, 3088, 3065, 3027, 3002, 1742, 1697, 1575, 1543, 1495, 1321, 1218, 1181, 1067, 1054, 777, 742, 702, 687 cm$^{-1}$;

$^1$H NMR (300 MHz, DMSO-d$_6$) δ 7.10–7.40, 6.92, 4.50–4.65, 3.66, 2.90–3.15;

MS (EI) m/z 338, 159, 133, 120, 103, 91, 88, 65.

EXAMPLE 2

Preparation of α-[[[(4,5-Dihydro-5-thioxo-1,3,4-thiadiazol-2-yl)amino]carbonyl]-amino]-N-methyl-(S)-benzenepropanamide.

13

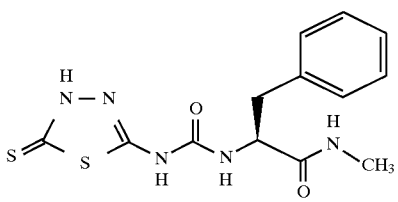

A saturated solution of methylamine in ethanol (50 mL) and N-[[(4,5-dihydro-5-thioxo-1,3,4-thiadiazol-2-yl)amino]carbonyl]-L-phenylalanine methyl ester (EXAMPLE 1; 0.770 g, 2.28 mmol) is stirred at room temperature for 6 days. The solution is concentrated, diluted with water, and acidified with 1N HCl. The resultant solids are filtered and dried to give 576 mg of the amide. Recrystallization from hot EtOAc/CH$_2$Cl$_2$/MeOH gives 390 mg (51%) of the desired product as a white solid (mp 234°–236° C.).

$[\alpha]^{25}_D$+72° (c 0.86, DMSO);

IR (mineral oil) 3320, 3152, 1686, 1651, 1640, 1578, 1553, 1546, 1494, 1055 cm$^{-1}$;

$^1$H NMR (300 MHz, DMSO-d$_6$) δ 13.83, 10.68, 8.10–8.20, 7.10–7.35, 6.85, 4.35–4.50, 2.98, 2.82, 2.59;

MS (EI) m/e 337, 306, 279, 205, 161, 159, 133, 120, 91.

EXAMPLE 3

Preparation of N-[[(4,5-Dihydro-5-thioxo-1,3,4-thiadiazol-2-yl)amino]carbonyl]-D-phenylalanine methyl ester.

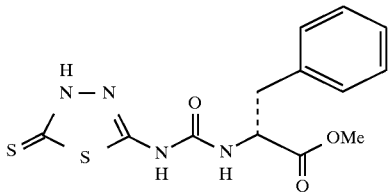

Following the general procedure outlined in EXAMPLE 1, and making non-critical variations but starting with D-phenylalanine methyl ester hydrochloride, the title compound is obtained (mp 110° C.).

$[\alpha]^{25}_D$−66° (c 0.96, CHCl$_3$);

IR (mineral oil) 3366, 3142, 3088, 3028, 1734, 1700, 1577, 1544, 1496, 1322, 1218, 1181, 1156, 1127, 1068, 1053, 1032, 792, 778, 752, 742, 702, 686, 640 cm$^{-1}$;

$^1$H NMR (300 MHz, CDCl$_3$) δ 12.75–13.20, 10.48, 7.20–7.40, 7.12, 5.76, 4.70–4.85, 3.75, 3.12;

MS (EI) m/z 338 (M$^+$), 306, 159, 133, 120, 103, 91, 88.

EXAMPLE 4

Preparation of α-[[[(4,5-Dihydro-5-thioxo-1,3,4-thiadiazol-2-yl)amino]carbonyl]-amino]-N-methyl-(R)-benzenepropanamide.

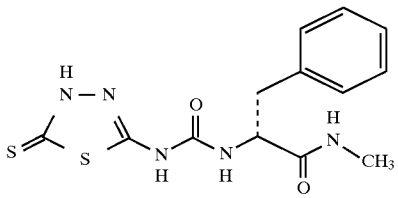

Following the general procedure outlined in EXAMPLE 2, and making non-critical variations but starting with N-[[(4,5-dihydro-5-thioxo-1,3,4-thiadiazol-2-yl)amino]carbonyl]-D-phenylalanine methyl ester (EXAMPLE 3), the title compound is obtained (mp 228° C.).

14

$[\alpha]^{25}_D$−36° (c 0.94, EtOH);

IR (mineral oil) 3376, 3317, 3264, 3152, 3064, 3029, 1687, 1651, 1638, 1577, 1556, 1494, 1321, 1286, 1257, 1242, 1230, 1055, 741, 699 cm$^{-1}$;

$^1$H NMR (300 MHz, DMSO-d$_6$) δ 13.83, 10.69, 8.10–8.20, 7.10–7.35, 6.83, 4.35–4.50, 2.99, 2.83, 2.59;

MS (FAB) m/z 338, 337, 205, 179, 120.

EXAMPLE 5

Preparation of α-[[[(4,5-Dihydro-5-thioxo-1,3,4-thiadiazol-2-yl)amino]carbonyl]-amino]-N-(phenylmethyl)-(S)-benzenepropanamide.

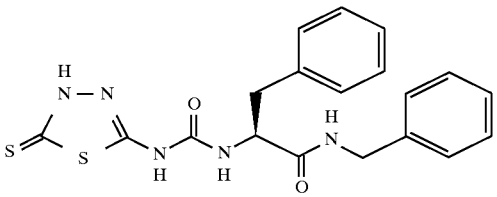

A solution of N-[[(4,5-dihydro-5-thioxo-1,3,4-thiadiazol-2-yl)amino]carbonyl]-L-phenylalanine methyl ester (EXAMPLE 1, 200 mg, 0.591 mmol) and benzylamine (1.0 mL) is stirred for 3 days at room temperature. The mixture is diluted with EtOAc and washed several times with 10% HCl and brine. The organic layer is dried (MgSO$_4$), filtered, and concentrated to give 214 mg of the amide. Recrystallization from hot CH$_2$Cl$_2$/hexane gives 150 mg (61%) of the title compound as a white solid (mp 198°–200° C.). Occasionally this reaction is carried out in EtOH or MeOH, especially when the amine used is methylamine. The solution is concentrated (if necessary) and either triturated with ether to give a solid (and remove excess amine) or partitioned between EtOAc and dilute HCl. Purification by flash chromatography and recrystallization is usually sufficient to provide analytically pure material.

$[\alpha]^{25}_D$+13° (c 0.46, DMSO);

IR (mineral oil) 3319, 3193, 3109, 3088, 3064, 3028, 1692, 1643, 1604, 1575, 1544, 1497, 1320, 1284, 1230, 1057, 1030, 740, 698, 645 cm$^{-1}$;

$^1$H NMR (300 MHz, DMSO-d$_6$) δ 13.83, 10.70, 8.65–8.80, 7.10–7.40, 6.8–6.95, 4.45–4.60, 4.20–4.40, 2.85–3.10;

MS (EI) m/z 413, 237, 163, 159, 133, 121, 120, 106, 91.

EXAMPLE 6

Preparation of α-[[[(4,5-Dihydro-5-thioxo-1,3,4-thiadiazol-2-yl)amino]carbonyl]-amino]-N-(phenylmethyl)-(S)-benzenepropanamide.

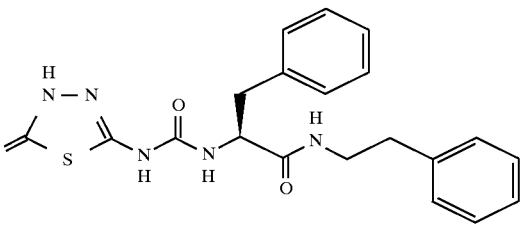

Following the general procedure outlined in EXAMPLE 5, and making non-critical variations but starting with phenethylamine, the title compound is obtained (mp 167°–170° C.).

$[\alpha]^{25}_D$+26° (c 0.45, DMSO);

IR (mineral oil) 3310, 3264, 3160, 3107, 3062, 3026, 1694, 1642, 1603, 1559, 1496, 1322, 1288, 1233, 1059, 776, 742, 698 cm$^{-1}$;

$^1$H NMR (300 MHz, DMSO-d$_6$) δ 13.83, 10.70, 8.25–8.40, 7.05–7.35, 6.75–6.90, 4.35–4.55, 2.70–3.05, 2.69;

MS (EI) m/z 306, 251, 177, 133, 121, 120, 105, 104, 91.

EXAMPLE 7

Preparation of α-[[[(4,5-Dihydro-5-thioxo-1,3,4-thiadiazol-2-yl)amino]carbonyl]-amino]-N-(2-pyridinylmethyl)-(S)-benzenepropanamide.

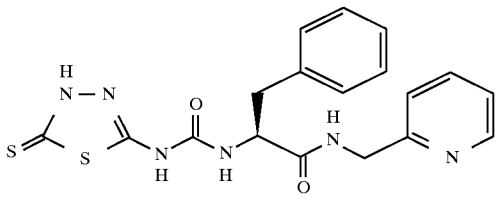

Following the general procedure outlined in EXAMPLE 5, and making non-critical variations but starting with 2-(aminomethyl)pyridine, the title compound is obtained (mp 159°–161° C.).

[α]$^{25}_D$+6° (c 0.42, DMSO);

IR (mineral oil) 3348, 3302, 3237, 3139, 3087, 3058, 3026, 2725, 1713, 1685, 1641, 1597, 1585, 1573, 1536, 1497, 1438, 1349, 1319, 1313, 1300, 1240, 1220, 1062, 1052, 1032, 1010, 772, 748, 730, 696, 642, 614 cm$^{-1}$;

$^1$H NMR (300 MHz, DMSO-d$_6$) δ 13.85, 10.72, 8.80–8.90, 8.51, 7.65–7.85, 7.15–7.35, 7.05–7.15, 6.80–6.95, 4.50–4.65, 4.30–4.45, 2.85–3.10;

MS (FAB) m/z 415, 414, 282, 256, 120, 109, 93.

EXAMPLE 8

Preparation of α-[[[(4,5-Dihydro-5-thioxo-1,3,4-thiadiazol-2-yl)amino]carbonyl]-amino]-N,N-dimethyl-(S)-benzenepropanamide.

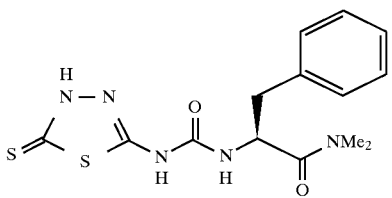

Following the general procedure outlined in EXAMPLE 5, and making critical variations but starting with 40% aqueous dimethylamine, the title compound is obtained (mp 196°–197° C.). [α]$^{25}_D$+24° (c 0.39, DMSO);

IR (mineral oil) 3332, 3167, 3129, 3063, 3027, 1693, 1622, 1576, 1547, 1495, 1422, 1405, 1320, 1283, 1231, 1065, 1054, 779, 745, 699, 637 cm$^{-1}$;

$^1$H NMR (300 MHz, DMSO-d$_6$) δ 13.86, 10.76, 7.10–7.35, 6.90–7.05, 4.85–5.00, 2.70–3.00, 2.88, 2.81.

EXAMPLE 9

Preparation of α-[[[(4,5-Dihydro-5-thioxo-1,3,4-thiadiazol-2-yl)amino]carbonyl]-amino]-(S)-benzenepropanamide.

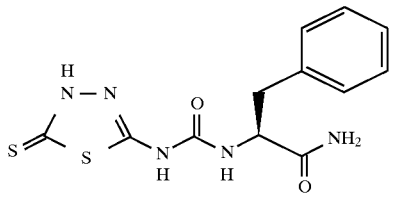

Following the general procedure outlined in EXAMPLE 5, and making non-critical variations but starting with EtOH saturated with ammonia, the title compound is obtained (mp 175°–177° C.).

[α]$^{25}_D$+82° (c 0.30, DMSO);

IR (mineral oil) 3459, 3391, 3320, 3192, 3085, 3062, 3028, 1682, 1666, 1604, 1570, 1541, 1496, 1418, 1319, 1259, 1241, 1068, 742, 699 cm$^{-1}$;

$^1$H NMR (300 MHz, DMSO-d$_6$) δ 11.17, 7.73, 7.15–7.35, 6.85–7.00, 4.40–4.55, 2.85–3.15.

EXAMPLE 10

Preparation of α-[[[(4,5-Dihydro-5-thioxo-1,3,4-thiadiazol-2-yl)amino]-carbonyl]amino]-N-(1-methylethyl)-(S)-benzenepropanamide.

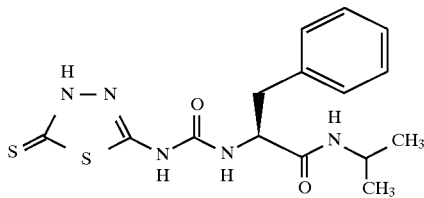

Following the general procedure outlined in EXAMPLE 5, and making non-critical variations but starting with isopropylamine, the title compound is obtained (mp 206°–211° C.).

[α]$^{25}_D$+20° (c 0.40, DMSO);

IR (mineral oil) 3270, 3121, 3027, 1691, 1641, 1557, 1493, 1319, 1287, 1236, 1129, 1065, 1053, 742, 697, 683, 648 cm$^{-1}$;

$^1$H NMR (300 MHz, DMSO-d$_6$) δ 13.83, 10.69, 8.06, 7.10–7.35, 6.85, 4.35–4.50, 3.70–3.85, 2.75–3.00, 1.04, 0.97.

EXAMPLE 11

Preparation of N-Butyl-α-[[[(4,5-dihydro-5-thioxo-1,3,4-thiadiazol-2-yl)amino]carbonyl]amino]-(S)-benzenepropanamide.

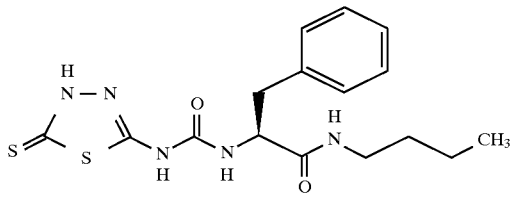

Following the general procedure outlined in EXAMPLE 5, and making non-critical variations but starting with butylamine, the title compound is obtained (mp 177°–179° C.).

[α]$^{25}_D$+42° (c 0.43, DMSO);

IR (mineral oil) 3319, 3105, 3088, 3064, 3028, 1702, 1639, 1575, 1549, 1495, 1320, 1284, 1227, 1053, 780, 741, 722, 699, 645 cm$^{-1}$;

$^1$H NMR (300 MHz, DMSO-d$_6$) δ 13.82, 10.68, 8.10–8.20, 7.10–7.35, 6.75–6.90, 4.35–4.50, 2.80–3.20, 1.10–1.40, 0.84.

EXAMPLE 12
Preparation of N-[[(4,5-Dihydro-5-thioxo-1,3,4-thiadiazol-2-yl)amino]carbonyl]-L-phenylalanine.

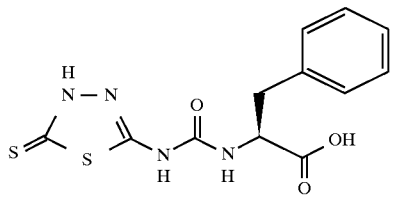

A mixture of N-[[(4,5-dihydro-5-thioxo-1,3,4-thiadiazol-2-yl)amino]carbonyl]-L-phenylalanine methyl ester (EXAMPLE 1; 528 mg, 1.56 mmol), MeOH (20 mL), H$_2$O (5.0 mL) and KOH (350 mg, 6.24 mmol) is stirred at room temperature for 16 hours. The solution is concentrated (to remove the MeOH), acidified with 10% HCl, and extracted with EtOAc (3×20 mL). The organic layers are dried (MgSO$_4$), filtered, and concentrated to give 490 mg (97%) of the title compound (mp 130° C.).

[α]$^{25}_D$+15° (c 0.46, DMSO);
IR (mineral oil) 3131, 3088, 3064, 3028, 2630, 1692, 1548, 1497, 1397, 1322, 1246, 1127, 1067, 1053, 772, 751, 735, 701 cm$^{-1}$;
$^1$H NMR (300 MHz, DMSO-d$_6$) δ 13.83, 13,0–13.25, 10.81, 7.15–7.35, 6.75–6.90, 4.40–4.55, 2.95–3.20;
MS (EI) m/z 306, 159, 128, 120, 92, 91, 83, 77, 74, 65.

EXAMPLE 13
Preparation of α-[[[(4,5-Dihydro-5-thioxo-1,3,4-thiadiazol-2-yl)amino]carbonyl]-amino]-N-methyl-(S)-1H-indole-3-propanamide.

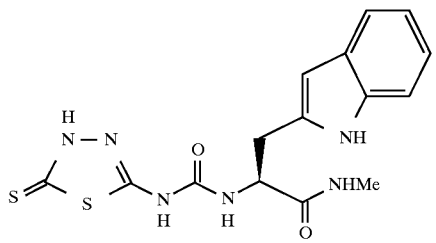

Following the general procedures outlined in EXAMPLE 5, and making non-critical variations but starting with Cbz-L-tryptophan methyl ester (prepared according to the procedure described in EXAMPLE 1), the title compound is obtained (mp 205°–210° C.).

[α]$^{25}_D$+62° (c 0.44, DMSO);
IR (mineral oil) 3319, 3186, 3103, 2729, 1696, 1640, 1542, 1414, 1340, 1316, 1280, 1227, 1161, 1126, 1096, 1054, 1011, 971, 742, 689 cm$^{-1}$;
$^1$H NMR (300 MHz, DMSO-d$_6$) δ 10.89, 8.10–8.20, 7.51, 7.33, 6.75–7.10, 4.35–4.50, 2.95–3.20, 2.57;
MS (FAB) m/z 377, 218, 200, 186, 139, 130, 103.

EXAMPLE 14
Preparation of (S)-1-[2-[[[(4,5-Dihydro-5-thioxo-1,3,4-thiadiazol-2-yl)amino]-carbonyl]amino]-1-oxo-3-phenylpropyl]-4-(phenylmethyl)-piperazine.

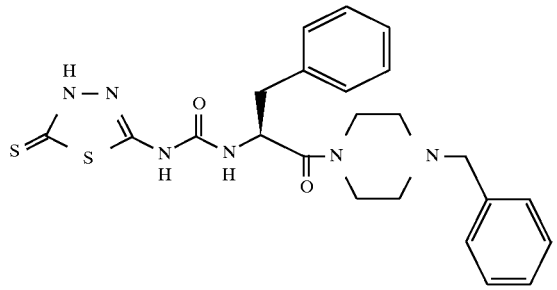

Following the general procedure outlined in EXAMPLE 5, and making non-critical variations but starting with benzylpiperazine, the title compound is obtained (mp 210°–213° C.).

[α]$^{25}_D$+13° (c 0.30, DMSO);
IR (mineral oil) 3343, 3118, 3086, 3061, 3029, 1687, 1612, 1576, 1551, 1493, 1319, 1267, 1225, 1060, 697 cm$^{-1}$;
1H NMR (300 MHz, DMSO-d$_6$) δ 13.70–13.95, 10.74, 7.10–7.45, 7.00, 4.90–5.00, 3.44, 3.15–3.55, 2.80–3.00, 2.15–2.40, 1.95–2.10;
MS (EI) m/z 349, 323, 306, 232, 159, 146, 134, 120, 91.

EXAMPLE 15
Preparation of (S)-1-[2-[[[(4,5-Dihydro-5-thioxo-1,3,4-thiadiazol-2-yl)amino]carbonyl]amino]-1-oxo-3-phenylpropyl]-4-(2-pyridinyl)piperazine.

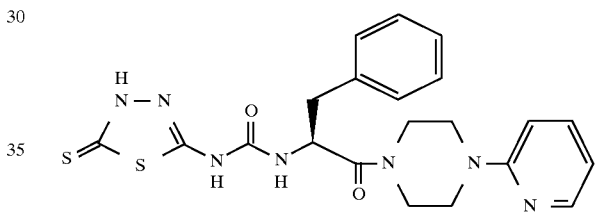

Following the general procedure outlined in EXAMPLE 5, and making non-critical variations but starting with 1-(2-pyridyl)piperazine, the title compound is obtained (mp 220°–222° C.).

[α]$^{25}_D$+24° (c 0.29, DMSO);
IR (mineral oil) 3354, 3186, 1685, 1613, 1596, 1579, 1536, 1436, 1314, 1283, 1269, 1241, 1219, 1057, 701 cm$^{-1}$;
1H NMR (300 MHz, DMSO-d$_6$) δ 13.85, 10.76, 8.10–8.15, 7.50–7.60, 7.15–7.35, 7.06, 6.81, 6.65–6.75, 4.95–5.05, 3.25–3.65, 3.10–3.20, 2.85–3.05;
MS (EI) m/z 336, 310, 219, 133, 121, 120, 107, 95.

EXAMPLE 16
Preparation of α-[[[(4,5-Dihydro-5-thioxo-1,3,4-thiadiazol-2-yl)amino]carbonyl]amino]-N-[(3,4-dimethoxyphenyl)methyl]-(S)-benzenepropanamide.

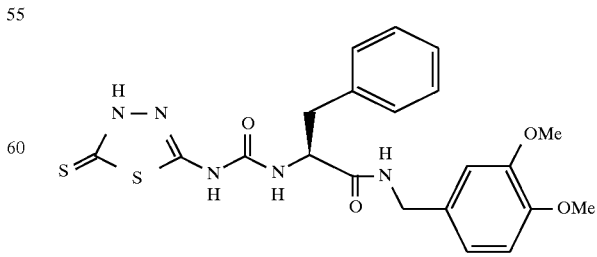

Following the general procedure outlined in EXAMPLE 5, and making non-critical variations but starting with veratrylamine, the title compound is obtained (mp 207°–210° C.).

[α]$^{25}_D$+20° (c 0.41, DMSO);

IR (mineral oil) 3308, 3291, 3250, 3221, 1692, 1628, 1608, 1579, 1554, 1519, 1445, 1270, 1235, 1060, 692 cm$^{-1}$;

1H NMR (300 MHz, DMSO-d$_6$) δ 13.83, 10.72, 8.60–8.75, 7.10–7.35, 6.80–6.95, 6.72, 4.45–4.55, 4.22, 3.73, 3.72, 3.03, 2.88.

EXAMPLE 17

Preparation of α-[[[(4,5-Dihydro-5-thioxo-1,3,4-thiadiazol-2-yl)amino]-carbonyl]amino]-N-(4-pyridinylmethyl)-(S)-benzenepropanamide.

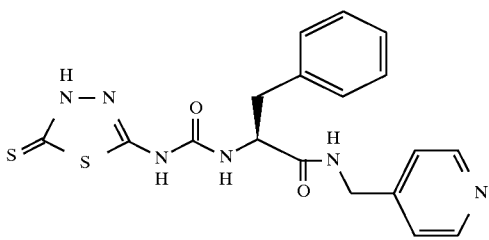

Following the general procedure outlined in EXAMPLE 5, and making non-critical variations but starting with 4-(aminomethyl)pyridine, the title compound is obtained (mp 208°–211° C.).

[α]$^{25}_D$–8° (c 0.56, DMSO);

IR (mineral oil) 3351, 3282, 1720, 1707, 1645, 1610, 1574, 1530, 1497, 1445, 1324, 1309, 1210, 1056, 702 cm$^{-1}$;

$^1$H NMR (300 MHz, DMSO-d$_6$) δ 13.86, 10.73, 8.75–8.90, 8.47, 7.05–7.40, 6.92, 4.50–4.65, 4.32, 3.05, 2.93;

MS (FAB) m/z 415, 414, 282, 256, 120, 93.

EXAMPLE 18

Preparation of α-[[[(4,5-Dihydro-5-thioxo-1,3,4-thiadiazol-2-yl)amino]carbonyl]-amino]-N-(3-pyridinylmethyl)-(S)-benzenepropanamide.

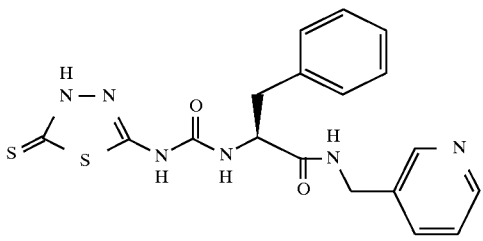

Following the general procedure outlined in EXAMPLE 5, and making non-critical variations but starting with 3-(aminomethyl)pyridine, the title compound is obtained (mp 99°–101° C.).

[α]$^{25}_D$+5° (c 0.39, DMSO);

IR (mineral oil) 3204, 3028, 1655, 1549, 1497, 1481, 1431, 1310, 1237, 1191, 1044, 1032, 745, 710, 639 cm$^{-1}$.

EXAMPLE 19

Preparation of α-[[[(4,5-Dihydro-5-thioxo-1,3,4-thiadiazol-2-yl)amino]carbonyl]-amino]-N-[2-(4-morpholinyl)ethyl]-(S)-benzenepropanamide.

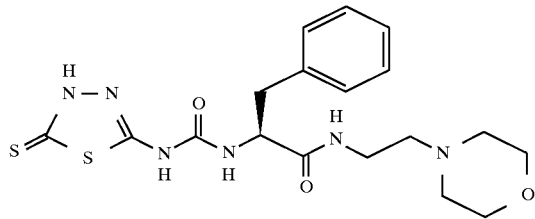

Following the general procedure outlined in EXAMPLE 5, and making non-critical variations but starting with 4-(2-aminoethyl)morpholine, the title compound is obtained (mp 165°–167° C.).

[α]$^{25}_D$+32° (c 0.37, DMSO);

IR (mineral oil) 3295, 1698, 1638, 1572, 1557, 1512, 1319, 1312, 1279, 1268, 1243, 1237, 1226, 1117, 698 cm$^{-1}$;

$^1$H NMR (300 MHz, DMSO-d$_6$) δ8.05–8.25, 7.05–7.40, 6.75–6.95, 4.35–4.55, 3.10–3.70, 3.00, 2.87, 2.20–2.50.

EXAMPLE 20

Preparation of α-[[[(4,5-Dihydro-5-thioxo-1,3,4-thiadiazol-2-yl)amino]carbonyl]-amino]-N-methyl-4-bromobenzenepropanamide.

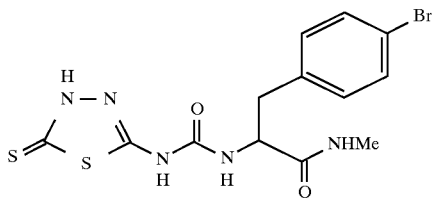

Following the general procedure outlined in EXAMPLE 5, and making non-critical variations but starting with N-[[(4,5-dihydro-5-thioxo-1,3,4-thiadiazol-2-yl)amino]carbonyl]-(4-bromophenyl)alanine methyl ester (prepared according to the procedure described in EXAMPLE 1), the title compound is obtained (mp 238°–241° C.).

IR (mineral oil) 3325, 3121, 3023, 1695, 1640, 1575, 1552, 1488, 1410, 1323, 1289, 1253, 1233, 1056, 1013 cm$^{-1}$;

$^1$H NMR (300 MHz, DMSO-d$_6$) δ 13.83, 10.71, 8.10–8.25, 7.48, 7.11, 6.80–6.95, 4.35–4.50, 2.97, 2.82, 2.59.

EXAMPLE 21

Preparation of (S)-1-[2-[[[(4,5-Dihydro-5-thioxo-1,3,4-thiadiazol-2-yl)amino]carbonyl]amino]-1-oxo-3-phenylpropyl]-4-(4-methoxyphenyl)piperazine.

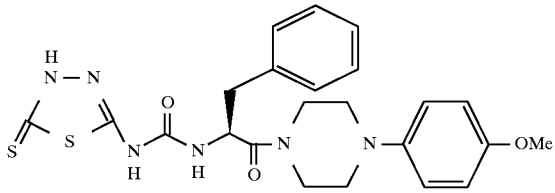

Following the general procedure outlined in EXAMPLE 5, and making non-critical variations but starting with 1-(4-methoxyphenyl)piperazine, the title compound is obtained (mp 201°–203° C.).

[α]$^{25}_D$+3° (c 0.34, DMSO);

IR (mineral oil) 3355, 3164, 1687, 1676, 1612, 1576, 1538, 1511, 1311, 1281, 1244, 1229, 1055, 1037, 700 cm$^{-1}$;

¹H NMR (300 MHz, DMSO-d₆) δ 13.85, 10.76, 7.15–7.35, 7.04, 6.75–6.90, 4.95–5.05, 3.69, 3.40–3.65, 2.75–3.05, 2.55–2.65;

MS (EI) m/z 498, 366, 340, 193.

EXAMPLE 22
Preparation of (S)-1-[2-[[[(4,5-Dihydro-5-thioxo-1,3,4-thiadiazol-2-yl)amino]-carbonyl]amino]-1-oxo-3-phenylpropyl]-4-(2-pyrimidinyl)-piperazine.

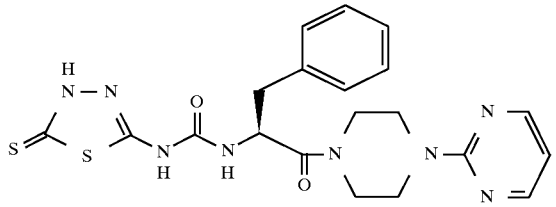

Following the general procedure outlined in EXAMPLE 5, and making non-critical variations but starting with 1-(2-pyrimidyl)piperazine, the title compound is obtained (mp 235°–237° C.).

[α]²⁵_D +12° (c 0.71, DMSO);

IR (mineral oil) 3357, 3171, 1685, 1611, 1585, 1549, 1537, 1496, 1358, 1319, 1282, 1260, 1220, 1058, 982 cm⁻¹;

¹H NMR (300 MHz, DMSO-d₆) δ 13.79, 10.70, 8.35, 7.10–7.30, 6.95–7.05, 6.46, 4.90–5.05, 3.15–3.80, 2.80–3.00;

MS (FAB) m/z 471, 470, 338, 313, 312, 167, 165, 121.

EXAMPLE 23
Preparation of (S)-1-[2-[[[(4,5-Dihydro-5-thioxo-1,3,4-thiadiazol-2-yl)amino]-carbonyl]amino]1-oxo-3-(pentafluorophenyl)propyl]-4-(2-pyridinyl)piperazine.

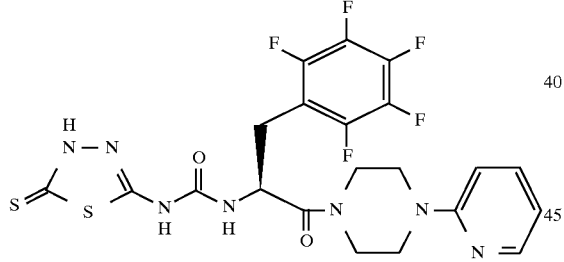

Following the general procedure outlined in EXAMPLE 5, and making non-critical variations but starting with N-[[(4,5-dihydro-5-thioxo-1,3,4-thiadiazol-2-yl)amino]carbonyl]-L-(pentafluorophenyl)alanine methyl ester (prepared according to the procedure described in EXAMPLE 1) and 1-(2-pyridyl)piperazine, the title compound is obtained (mp 233°–235° C.).

[α]²⁵_D +36° (c 0.62, DMSO);

IR (mineral oil) 3361, 1706, 1626, 1593, 1576, 1534, 1522, 1504, 1480, 1436, 1326, 1282, 1240, 1216, 1020 cm⁻¹;

¹H NMR (300 MHz, DMSO-₆) δ 13.83, 10.75, 8.05–8.15, 7.50–7.60, 7.10, 6.85, 6.67, 5.05–5.15, 3.40–3.80, 3.15–3.30, 2.90–3.05.

EXAMPLE 24
Preparation of (S)-N-[[(4,5-Dihydro-5-thioxo-1,3,4-thiadiazol-2-yl)amino]carbonyl]-2-phenylglycine methyl ester.

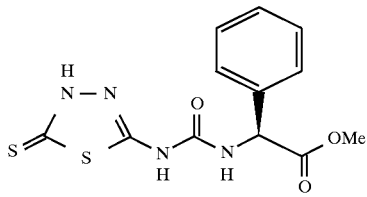

Following the general procedure outlined in EXAMPLE 1, and making non-critical variations but starting with (S)-2-phenylglycine methyl ester hydrochloride, the title compound is obtained (mp 137°–139° C.).

[α]²⁵_D +188° (c 0.99, DMSO);

IR (mineral oil) 3272, 3219, 1739, 1693, 1653, 1575, 1546, 1484, 1439, 1321, 1298, 1260, 1213, 1068, 1053 cm⁻¹;

1H M///R (300 Hz, MSO-d₆) δ 13.85, 10.63, 7.56, 7.25–7.50, 5.37, 3.64.

EXAMPLE 25
Preparation of α-[[[(4,5-Dihydro-5-thioxo-1,3,4-thiadiazol-2-yl)amino]carbonyl]amino]-N-methyl-(S)-benzeneacetamide.

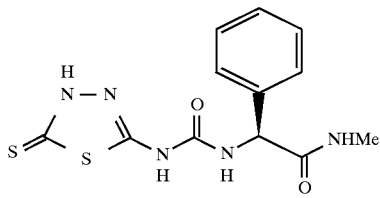

Following the general procedure outlined in EXAMPLE 5, and making non-critical variations but starting with (S)-N-[[(4,5-dihydro-5-thioxo-1,3,4-thiadiazol-2-yl)amino]carbonyl]-2-phenylglycine methyl ester (EXAMPLE 24), the title compound is obtained (mp 240°–241° C.).

[α]²⁵_D +12° (c 0.53, DMSO);

IR (mineral oil) 3320, 3231, 3174, 3088, 1698, 1640, 1584, 1565, 1549, 1495, 1412, 1336, 1229, 710, 700 cm⁻¹;

¹H NMR (300 MHz, DMSO-d₆) δ 13.80, 10.70, 8.30–8.40, 7.55, 7.20–7.40, 5.25, 2.57;

MS (EI) m/z 323, 159, 133, 132, 107, 106, 104, 83, 79, 77, 58.

EXAMPLE 26
Preparation of α-[[[(4,5-Dihydro-5-thioxo-1,3,4-thiadiazol-2-yl)amino] carbonyl]amino]-4-fluoro-N-methyl-(S)-benzenepropanamide.

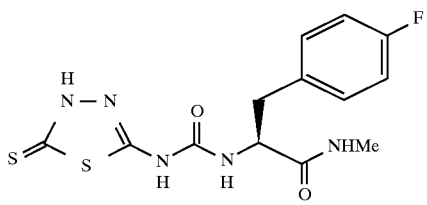

Following the general procedure outlined in EXAMPLE 5, and making non-critical variations but starting with N-[[(4,5-dihydro-5-thioxo-1,3,4-thiadiazol-2-yl)amino] carbonyl]-L-(4-fluorophenyl)alanine methyl ester (prepared according to the procedure described in EXAMPLE 1), the title compound is obtained (mp 225°–227° C.).

[α]$^{25}_D$+62° (c 0.81, DMSO);

IR (mineral oil) 3310, 3226, 3133, 1694, 1633, 1600, 1579, 1544, 1509, 1491, 1325, 1258, 1242, 1227, 1056 cm$^{-1}$;

$^1$H NMR (300 MHz, DMSO-d$_6$) δ 13.78, 10.66, 8.05–8.15, 7.00–7.20, 6.81, 4.30–4.45, 2.75–3.00, 2.56.

EXAMPLE 27
Preparation of (S)-1-[2-[[[(4,5-Dihydro-5-thioxo-1,3,4-thiadiazol-2-yl)amino]-carbonyl]amino]-1-oxo-3-(4-fluorophenyl)propyl]-4-(2-pyridinyl)piperazine.

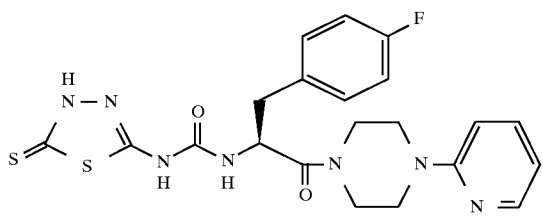

Following the general procedure outlined in EXAMPLE 5, and making non-critical variations but starting with N-[[(4,5-dihydro-5-thioxo-1,3,4-thiadiazol-2-yl)amino]carbonyl]-L-(4-fluorophenyl)alanine methyl ester (prepared similarly to that described in EXAMPLE 1) and 1-(2-pyridyl)piperazine, the title compound is obtained (mp 240°–241.5° C.).

[α]$^{25}_D$+11° (c 0.43, DMSO);

IR (mineral oil) 3363, 3168, 1681, 1616, 1596, 1579, 1539, 1509, 1435, 1314, 1267, 1242, 1225, 1059, 778 cm$^{-1}$;

$^1$H NMR (300 MHz, DMSO-d$_6$) δ 13.81, 10.72, 8.05–8.15, 7.45–7.60, 6.95–7.25, 6.80, 6.60–6.70, 4.90–5.50, 3.20–3.70, 2.80–3.00.

EXAMPLE 28
Preparation of 2-[[[(4,5-Dihydro-5-thioxo-1,3,4-thiadiazol-2-yl)amino]-carbonyl]amino]-4-methyl-N-(2-phenylethyl)-(S)-pentanamide.

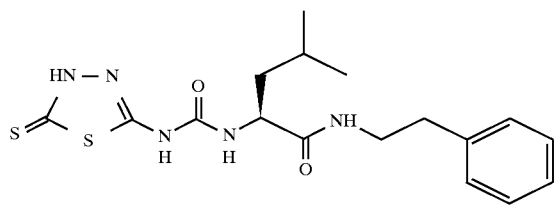

Following the general procedure outlined in EXAMPLE 5, and making non-critical variations but starting with N-[[(4,5-dihydro-5-thioxo-1,3,4-thiadiazol-2-yl)amino]carbonyl]-L-leucine methyl ester (prepared according to the procedure described in EXAMPLE 1) and phenethylamine, the title compound is obtained (mp 215°–217° C., decomposition).

[α]$^{25}_D$-43° (c 0.83, DMSO);

IR (mineral oil) 3291, 3247, 3173, 3107, 1694, 1642, 1567, 1496, 1320, 1234 cm$^{-1}$;

$^1$H NMR (300 MHz, DMSO-d$_6$) δ 13.84, 10.60, 8.28, 7.15–7.30, 6.80, 4.10–4.25, 3.20–3.35, 2.71, 1.30–1.55, 0.85, 0.84;

MS (EI) m/z 393, 272, 261, 159, 133, 104, 91, 86.

EXAMPLE 29
Preparation of 2-[[[(4,5-Dihydro-5-thioxo-1,3,4-thiadiazol-2-yl)amino]carbonyl]amino]-4-methyl-N-(phenylmethyl)-(S)-pentanamide.

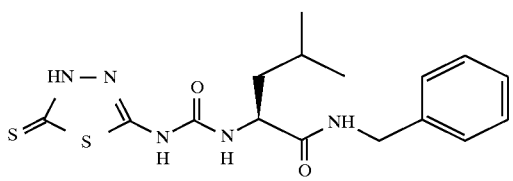

Following the general procedure outlined in EXAMPLE 5, and making non-critical variations but starting with N-[[(4,5-dihydro-5-thioxo-1,3,4-thiadiazol-2-yl)amino]carbonyl]-L-leucine methyl ester (EXAMPLE 28) and benzylamine, the title compound is obtained (mp 206°–208° C.).

[α]$^{25}_D$-41° (c 0.55, DMSO);

IR (mineral oil) 3197, 3145, 3086, 3066, 1690, 1633, 1580, 1541, 1240, 1228 cm$^{-1}$;

$^1$H NMR (300 MHz, DMSO-d$_6$) δ 13.83, 10.62, 8.74, 7.20–7.35, 6.87, 4.20–4.35, 1.40–1.60, 0.89, 0.87.

EXAMPLE 30
Preparation of N-[[(4,5-Dihydro-5-thioxo-1,3,4-thiadiazol-2-yl)amino]carbonyl]-O-methyl-L-tyrosine methyl ester.

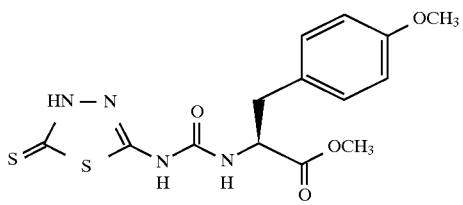

Following the general procedure outlined in EXAMPLE 1, and making non-critical variations but starting with O-methyl-L-tyrosine methyl ester, the title compound is obtained (mp 117°–120° C., decomposition).

[α]$^{25}_D$+69° (c 0.91, DMSO);

IR (mineral oil) 1744, 1698, 1576, 1542, 1513, 1446, 1320, 1302, 1250, 1219 cm$^{-1}$;

$^1$H NMR (300 MHz, DMSO-d$_6$) δ 13.86, 10.83, 7.08, 6.87, 6.75–6.85, 4.45–4.60, 3.72, 3.66, 2.90–3.10;

MS (EI) m/z 368, 336, 192, 176, 159, 150, 133, 122, 121, 77.

EXAMPLE 31
Preparation of α-[[[(4,5-Dihydro-5-thioxo-1,3,4-thiadiazol-2-yl)amino]-carbonyl]amino]-4-methoxy-N-methyl-(S)-benzenepropanamide.

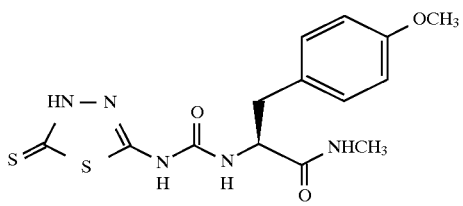

Following the general procedure outlined in EXAMPLE 5, and making non-critical variations but starting with N-[[(4,5-dihydro-5-thioxo-1,3,4-thiadiazol-2-yl)amino]carbonyl]-O-methyl-L-tyrosine methyl ester (EXAMPLE 30), the title compound is obtained (mp 232°–233° C.).

[α]$^{25}_D$+90° (c 0.91, DMSO);

IR (mineral oil) 3312, 1692, 1639, 1548, 1511, 1322, 1251, 1227, 1055 cm$^{-1}$;

$^1$H NMR (300 MHz, DMSO-d$_6$) δ 13.82, 10.69, 8.05–8.15, 7.06, 6.86, 6.75–6.90, 4.30–4.40, 3.71, 2.92, 2.77, 2.59.

EXAMPLE 32

Preparation of N-[[(4,5-Dihydro-5-thioxo-1,3,4-thiadiazol-2-yl)amino]carbonyl]-L-(4-nitrophenyl)alanine methyl ester.

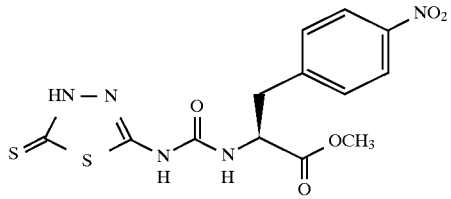

Following the general procedure outlined in EXAMPLE 1, and making non-critical variations but starting with L-4-nitrophenylalanine methyl ester hydrochloride, the title compound is obtained (mp 149°–152° C., decomposition).

[α]$^{25}_D$+65° (c 1.00, DMSO);

IR (mineral oil) 1695, 1659, 1591, 1550, 1518, 1512, 1349, 1343, 1328, 1216 cm$^{-1}$;

$^1$H NMR (300 MHz, DMSO-d$_6$) δ 13.85, 10.89, 8.18, 7.49, 7.06, 4.60–4.70, 3.68, 3.10–3.30;

MS (FAB) m/z 384, 236, 225, 134.

EXAMPLE 33

Preparation of α-[[[(4,5-Dihydro-5-thioxo-1,3,4-thiadiazol-2-yl)amino]carbonyl]amino]-N-methyl-4-nitro-(S)-benzenepropanamide.

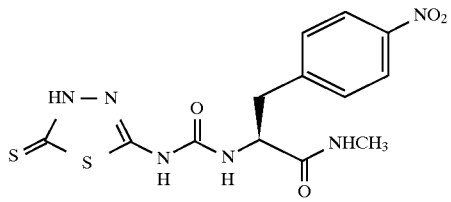

Following the general procedure outlined in EXAMPLE 5, and making non-critical variations but starting with N-[[(4,5-dihydro-5-thioxo-1,3,4-thiadiazol-2-yl)amino]carbonyl]-L-(4-nitrophenyl)alanine methyl ester (EXAMPLE 32), the title compound is obtained (mp 228°–230° C.).

[α]$^{25}_D$+114° (c 0.93, DMSO);

IR (mineral oil) 3313, 1695, 1639, 1579, 1544, 1518, 1492, 1345, 1324, 1052 cm$^{-1}$;

$^1$H NMR (300 MHz, DMSO-d$_6$) δ 13.83, 10.71, 8.15–8.25, 8.17, 7.44, 6.94, 4.40–4.55, 3.14, 3.00, 2.60;

MS (FAB) m/z 383, 250, 236, 224, 208, 160, 134.

EXAMPLE 34

Preparation of α-[[[(4,5-Dihydro-5-thioxo-1,3,4-thiadiazol-2-yl)amino]carbonyl]amino]-4-nitro-N-(2-phenylethyl)-(S)-benzenepropanamide.

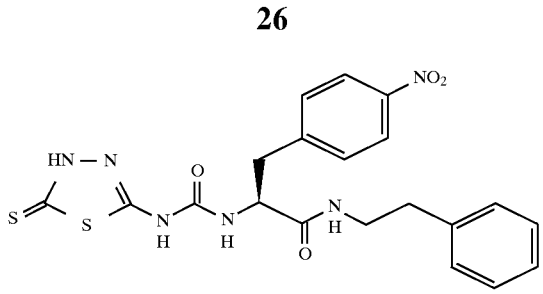

Following the general procedure outlined in EXAMPLE 5, and making non-critical variations but starting with N-[[(4,5-dihydro-5-thioxo-1,3,4-thiadiazol-2-yl)amino]carbonyl]-L-(4-nitrophenyl)alanine methyl ester (EXAMPLE 32) and phenethylamine, the title compound is obtained (mp 154° C., decomposition).

[α]$^{25}_D$+56° (c 0.97, DMSO);

IR (mineral oil) 3290, 3172, 3083, 3059, 3025, 1685, 1650, 1605, 1520, 1497, 1345, 1316, 1236, 1216, 698 cm$^{-1}$;

$^1$H NMR (300 MHz, DMSO-d$_6$) δ 11.19, 8.38, 8.13, 7.15–7.40, 7.04, 4.50–4.60, 3.20–3.45, 3.12, 2.98, 2.71;

MS (FAB) m/z 473, 472, 462, 359, 314, 122, 121.

EXAMPLE 35

Preparation of N-Butyl-α-[[[(4,5-dihydro-5-thioxo-1,3,4-thiadiazol-2-yl)amino]carbonyl]amino]-4-nitro-(S)-benzenepropanamide.

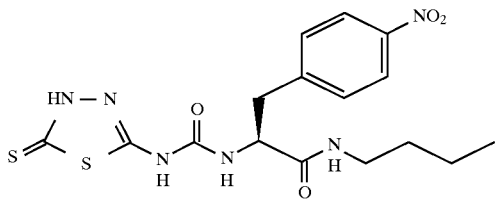

Following the general procedure outlined in EXAMPLE 5, and making non-critical variations but starting with N-[[(4,5-dihydro-5-thioxo-1,3,4-thiadiazol-2-yl)amino]carbonyl]-L-(4-nitrophenyl)alanine methyl ester (EXAMPLE 32) and butylamine, the title compound is obtained (mp 195° C., decomposition).

[α]$^{25}_D$+58° (c 0.90, DMSO);

IR (mineral oil) 3297, 3167, 3109, 1693, 1644, 1606, 1574, 1544, 1522, 1494, 1345, 1319, 1284, 1231, 692 cm$^{-1}$;

$^1$H NMR (300 MHz, DMSO-d$_6$) δ 13.84, 11.17, 10.71, 8.10–8.30, 8.17, 7.46, 6.90–7.15, 4.45–4.60, 2.90–3.15, 1.10–1.35, 0.82;

MS (FAB) m/z 425, 267, 266, 236, 165, 160, 134, 74, 57.

EXAMPLE 36

Preparation of (S)-4-[2-[[[(4,5-Dihydro-5-thioxo-1,3,4-thiadiazol-2-yl)amino]carbonyl]amino]-1-oxo-3-phenylpropyl]morpholine.

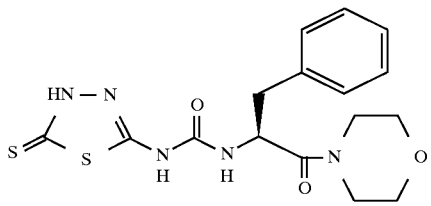

Following the general procedure outlined in EXAMPLE 5, and making non-critical variations but starting with morpholine, the title compound is obtained (mp 213°–216° C.).

$[\alpha]^{25}_D$ -23° (c 0.99, DMSO);

IR (mineral oil) 3353, 1703, 1616, 1578, 1532, 1442, 1326, 1291, 1218, 1107

$^1$H NMR (300 MHz, DMSO-d$_6$) δ 13.84, 10.76, 7.15–7.35, 7.02, 4.90–5.00, 2.80–3.60.

EXAMPLE 37

Preparation of α-[[[(4,5-Dihydro-5-thioxo-1,3,4-thiadiazol-2-yl)amino]carbonyl]amino]-N-(4-phenylbutyl)-(S)-benzenepropanamide.

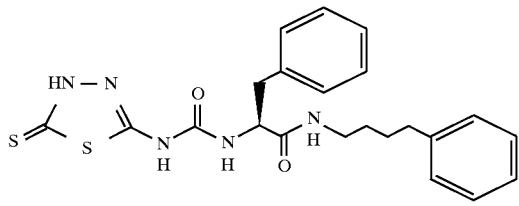

Following the general procedure outlined in EXAMPLE 5, and making non-critical variations but starting with phenbutylamine, the title compound is obtained (mp 184° C., decomposition).

$[\alpha]^{25}_D$ +28° (c 0.99, DMSO);

IR (mineral oil) 3311, 3107, 1693, 1640, 1575, 1552, 1495, 1319, 1232, 698 cm$^{-1}$;

$^1$H NMR (300 MHz, DMSO-d$_6$) δ 13.81, 10.67, 8.17, 7.10–7.30, 6.84, 4.35–4.50, 3.00–3.15, 2.96, 2.84, 2.50–2.60, 1.45–1.60, 1.25–1.45.

EXAMPLE 38

Preparation of N-Cyclohexylmethyl-α-[[[(4,5-Dihydro-5-thioxo-1,3,4-thiadiazol-2-yl)amino]carbonyl]amino]-(S)-benzenepropanamide.

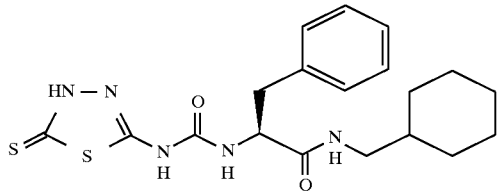

Following the general procedure outlined in EXAMPLE 5, and making non-critical variations but starting with aminomethylcyclohexane, the title compound is obtained (mp 185° C., decomposition).

$[\alpha]^{25}_D$ +26° (c 0.95, DMSO);

IR (mineral oil) 3333, 1704, 1637, 1636, 1579, 1550, 1496, 1451, 1225, 698 cm$^{-1}$;

$^1$H NMR (300 MHz, DMSO-d$_6$) δ 13.82, 10.71, 8.15, 7.10–7.30, 6.80–6.90, 4.40–4.50, 2.75–3.00, 1.50–1.70, 1.20–1.40, 1.00–1.20, 0.70–0.90.

EXAMPLE 39

Preparation of (S)-4-[2-[[[(4,5-Dihydro-5-thioxo-1,3,4-thiadiazol-2-yl)amino]carbonyl]amino]-1-oxo-3-phenylpropyl]pyrrolidine.

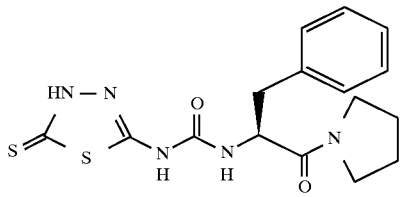

Following the general procedure outlined in EXAMPLE 5, and making non-critical variations but starting with pyrrolidine, the title compound is obtained (mp 185° C., decomposition).

$[\alpha]^{25}_D$ +26° (c 1.01, DMSO);

IR (mineral oil) 3325, 3161, 3125, 3024, 1694, 1615, 1576, 1542, 1317, 1227 cm$^{-1}$;

$^1$H NMR (300 MHz, DMSOd6) δ 13.84, 10.70, 7.10–7.35, 7.02, 4.55–4.70, 3.40–3.50 3.15–3.40, 2.80–3.05, 1.60–1.85.

EXAMPLE 40

Preparation of (S)-4-[2-[[[(4,5-Dihydro-5-thioxo-1,3,4-thiadiazol-2-yl)amino]carbonyl]amino]-1-oxo-3-phenylpropyl]-thiomorpholine.

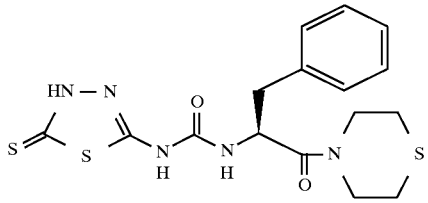

Following the general procedure outlined in EXAMPLE 5, and making non-critical variations but starting with thiomorpholine, the title compound is obtained (mp 210°–214° C., decomposition).

$[\alpha]^{25}_D$ +4° (c 0.99, DMSO);

IR (mineral oil) 3341, 3195, 3135, 1691, 1612, 1577, 1543, 1441, 1320, 1219 cm$^{-1}$;

$^1$H NMR (300 MHz, DMSO-d$_6$) δ 13.85, 10.72, 7.15–7.35, 7.02, 4.85–5.00, 3.60–3.80, 2.90, 2.35–2.60, 2.10–2.25.

EXAMPLE 41

Preparation of α-[[[(4,5-Dihydro-5-thioxo-1,3,4-thiadiazol-2-yl)amino]-carbonyl]amino]-N-(3-hydroxypropyl)-(S)-benzenepropanamide.

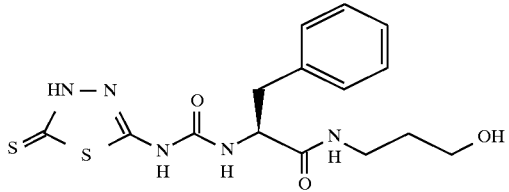

Following the general procedure outlined in EXAMPLE 5, and making non-critical variations but starting with 3-aminopropanol, the title compound is obtained (mp 125° C., decomposition).

$[\alpha]^{25}_D$ +31° (c 0.99, DMSO);

IR (mineral) 3319, 3103, 1701, 1640, 1575, 1544, 1496, 1321, 1231, 1064 cm$^{-1}$;

$^1$H NMR (300 MHz, DMSO-d$_6$) δ 13.82, 10.69, 8.18, 7.10–7.35, 6.85, 4.35–4.50, 3.20–3.40, 3.00–3.20, 2.97, 2.84, 1.45–1.55.

EXAMPLE 42

Preparation of N-[[(4,5-Dihydro-5-thioxo-1,3,4-thiadiazol-2-yl)amino]carbonyl]-L-phenylalanyl-β-alanine ethyl ester.

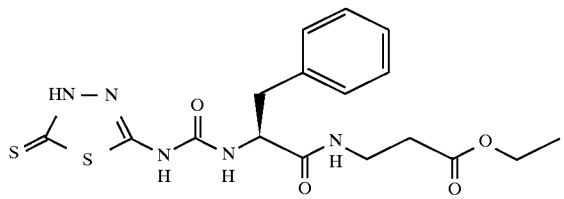

Triethylamine (1.16 mL, 8.33 mmol) is added to a stirred solution of N-[[(4,5-dihydro-5-thioxo-1,3,4-thiadiazol-2-yl)amino]carbonyl]-L-phenylalanine methyl ester (EXAMPLE 1; 402 mg, 1.19 mmol) and β-alanine ethyl ester hydrochloride (914 mg, 5.95 mmol) in EtOH (7 mL) and stirred for 2 days. After workup (EtOAc, 10% HCl, Na$_2$SO$_4$), 268 mg (53%) of the title compound is recovered as a powdery white solid (mp 205°–207° C.).

$[\alpha]^{25}_D$+8° (c 0.99, DMSO);

IR (mineral) 3318, 3210, 1714, 1693, 1639, 1577, 1548, 1378, 1219, 1204 cm$^{-1}$;

$^1$H NMR (300 MHz, DMSO-d$_6$) δ 13.82, 10.70, 8.35, 7.10–7.35, 6.82, 4.35–4.50, 4.06, 3.20–3.40, 2.97, 2.82, 2.41, 1.18;

MS (FAB) m/z 424, 279, 265, 236, 160, 146, 134, 133, 120, 118.

EXAMPLE 43

Preparation of N-[[[(4,5-Dihydro-5-thioxo-1,3,4-thiadiazol-2-yl)amino]carbonyl]-L-phenylalanyl-N-methyl-β-alaninamide.

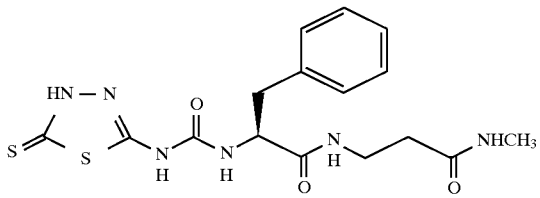

Following the general procedure outlined in EXAMPLE 5, and making non-critical variations but starting with N-[[(4,5-Dihydro-5-thioxo-1,3,4-thiadiazol-2-yl)amino]carbonyl]-L-phenylalanyl-β-alanine ethyl ester (EXAMPLE 42), the title compound is obtained (mp 211°–212° C.).

$[\alpha]^{25}_D$+1° (c 1.03, DMSO);

IR (mineral oil) 3341, 3299, 3110, 1697, 1641, 1581, 1533, 1476, 1451, 1319 cm$^{-1}$;

$^1$H NMR (300 MHz, DMSO-d$^6$) δ 13.82, 10.69, 8.28, 7.75–7.85, 7.10–7.30, 6.81, 4.35–4.50, 3.15–3.40, 2.97, 2.82, 2.57, 2.21;

MS (FAB) m/z 409, 276, 250, 160, 129, 120.

EXAMPLE 44

Preparation of N-[[[(4,5-Dihydro-5-thioxo-1,3,4-thiadiazol-2-yl)amino]carbonyl]-L-phenylalanyl-β-alanine.

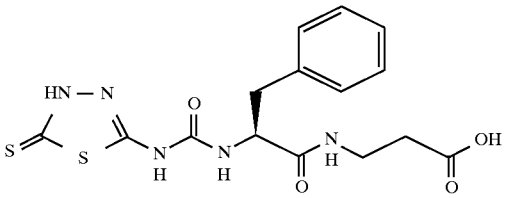

Potassium hydroxide (281 mg, 5.01 mmol) is dissolved in H$_2$O (5 mL) and added to a stirred solution of N-[[(4,5-Dihydro-5-thioxo-1,3,4-thiadiazol-2-yl)amino]carbonyl]-L-phenylalanyl-β-alanine ethyl ester (EXAMPLE 42; 530 mg, 1.25 mmol) in MeOH (10 mL). After 3 days, aqueous workup (EtOAc, 10% HCl, Na$_2$SO$_4$) gives 174 mg (35%) of the title compound as a white, powdery solid (216° C., decomposition).

$[\alpha]^{25}_D$+0.4° (c 1.01, DMSO);

IR (mineral oil) 3174, 3086, 1718, 1647, 1575, 1555, 1444, 1231, 1207, 1200 cm$^{-1}$;

$^1$H NMR (300 MHz, DMSO-d$_6$) δ 13.81, 12.28, 10.70, 8.33, 7.10–7.35, 6.82, 4.35–4.50, 3.15–3.40, 2.98, 2.83, 2.35;

MS (FAB) m/z 396, 237, 160, 120.

EXAMPLE 45

Preparation of N-[[[(4,5-Dihydro-5-thioxo-1,3,4-thiadiazol-2-yl)amino]carbonyl]-O-[(1,1-dimethylethyl)dimethylsilyl]-L-serine methyl ester.

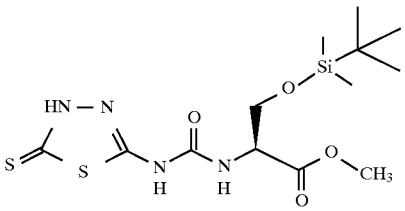

Following the general procedure outlined in EXAMPLE 1, and making non-critical variations but starting with O-(tert-butyldimethylsilyl)-L-serine methyl ester, the title compound is obtained.

$[\alpha]^{25}_D$+29° (c 1.00, DMSO);

IR (mineral oil) 1697, 1668, 1578, 1542, 1490, 1349, 1322, 1259, 1212, 1108, 1075, 1058, 836, 779 cm$^{-1}$;

$^1$H NMR (300 MHz, DMSO-d$_6$) δ 6.89, 4.35–4.50, 3.88, 3.66, 0.82, 0.01, –0.01;

MS (FAB) m/z 393, 335, 260, 234, 160, 134, 133, 102, 75, 73.

EXAMPLE 46

Preparation of 2-[[[(4,5-Dihydro-5-thioxo-1,3,4-thiadiazol-2-yl)amino]carbonyl]amino]-3-[(1,1-dimethylethyl)-dimethylsilyloxy]-N-methyl-(S)-propanamide.

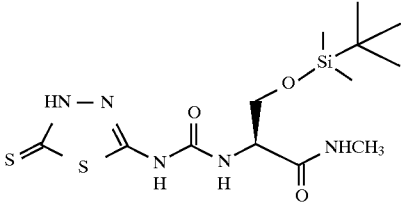

Following the general procedure outlined in EXAMPLE 5, and making non-critical variations but starting with 2-[[

[(4,5-dihydro-5-thioxo-1,3,4-thiadiazol-2-yl)amino]carbonyl]amino]-3-[(1,1-dimethylethyl)-dimethylsilyloxy]-N-methyl-(S)-propanamide (EXAMPLE 45), the title compound is obtained (mp 213°–214° C.).

[α]$^{25}_D$+24° (c 0.85, DMSO);

IR (mineral oil) 3274, 3181, 1689, 1641, 1586, 1550, 1526, 1490, 1321, 1254, 1222, 1121, 1083, 838, 779 cm$^{-1}$;

$^1$H NMR (300 MHz, DMS-d$_6$) δ 7.95–8.10, 6.80–6.90, 4.15–4.25, 3.73, 2.58, 0.81, –0.01, –0.02.

EXAMPLE 47

Preparation of N-[[(4,5-Dihydro-5-thioxo-1,3,4-thiadiazol-2-yl)amino]carbonyl]-O-[(1,1-dimethylethyl)dimethylsilyl]-L-tyrosine methyl ester.

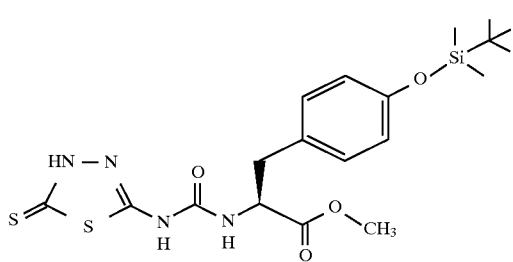

Following the general procedure outlined in EXAMPLE 1, and making non-critical variations but starting with O-(tert-butyldimethylsilyl)-L-tyrosine methyl ester, the title compound is obtained (mp 139°–142° C.).

[α]$^{25}_D$+65° (c 1.01, DMSO);

IR (mineral oil) 3382, 1726, 1689, 1575, 1542, 1512, 1329, 1285, 1272, 1256, 1215, 1051, 923, 839, 780 cm$^{-1}$;

$^1$H NMR (300 MHz, DMS$_6$) δ 7.02, 6.87, 6.74, 4.40–4.55, 3.62, 2.85–3.05, 0.91, 0.14;

MS (EI) m/z 411, 379, 292, 250, 223, 222, 221, 159, 107, 83, 73, 59.

EXAMPLE 48

Preparation of α-[[[(4,5-Dihydro-5-thioxo-1,3,4-thiadiazol-2-yl)amino]carbonyl]amino]-4-hydroxy-N-methyl-(S)-benzenepropanamide.

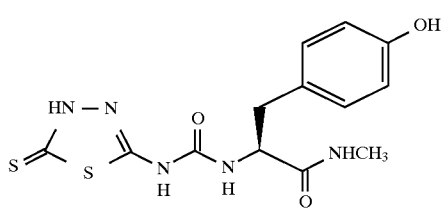

A solution of N-[[(4,5-Dihydro-5-thioxo-1,3,4-thiadiazol-2-yl)amino]carbonyl]-O-[(1,1-dimethylethyl)dimethylsilyl]-L-tyrosine methyl ester (EXAMPLE 47; 2.42 g, 5.16 mmol), THF (75 mL), and tetrabutylammonium fluoride (12.4 mL, 12.4 mmol, 1.0M in THF) is stirred at room temperature for 1.5 hours and then concentrated. The residue is partitioned between dilute HCl and EtOAc (several times). The organic layers are dried (Na$_2$SO$_4$), filtered, and concentrated. The residue is purified by silica gel chromatography (4% MeOHCH$_2$Cl$_2$) to give 1.52 g (83%) of the intermediate phenol.

Following the general procedure outlined in EXAMPLE 5, and making non-critical variations but starting with the crude phenol, the title compound is obtained (mp 198°–200° C.).

[α]$^{25}_D$+72° (c 1.00, DMSO);

IR (mineral oil) 3371, 3312, 3127, 1705, 1693, 1640, 1578, 1550, 1516, 1491, 1324, 1285, 1260, 1229, 1053 cm$^{-1}$;

$^1$H NMR (300 MHz, DMS$_6$) δ 13.75, 10.65, 9.20, 7.95–8.10, 6.91, 6.77, 6.63, 4.20–4.35, 2.84, 2.69, 2.55.

EXAMPLE 49

Preparation of α-[[[(4,5-Dihydro-5-thioxo-1,3,4-thiadiazol-2-yl)amino]-carbonyl]amino]-N-(piperonyl)-(S)-benzenepropanamide.

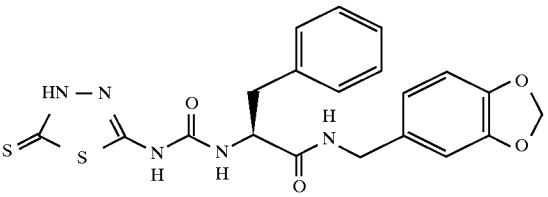

Following the general procedure outlined in EXAMPLE 5, and making non-critical variations but starting with piperonylamine, the title compound is obtained (mp 213°–213° C.).

IR (mineral oil) 3199, 3127, 3085, 1692, 1633, 1579, 1547, 1503, 1488, 1444, 1260, 1250, 1233, 1043, 700 cm$^{-1}$;

$^1$H NMR (300 MHz, DMSO-d$_6$) δ 13.83, 10.71, 8.64, 7.10–7.35, 6.80–6.95, 6.84, 6.74, 6.67, 5.99, 4.40–4.55, 4.10–4.25, 2.80–3.10.

EXAMPLE 50

Preparation of (S)-1-[2-[[[(4,5-Dihydro-5-thioxo-1,3,4-thiadiazol-2-yl)amino]carbonyl]amino]-1-oxo-3-phenylpropyl]-4-phenylpiperazine.

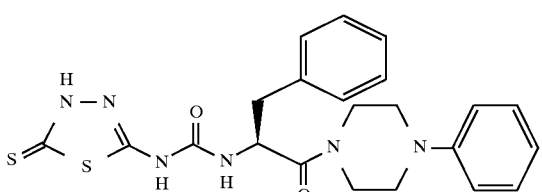

Following the general procedure outlined in EXAMPLE 5, and making non-critical variations but starting with 1-phenylpiperazine, the title compound is obtained (mp 210°–211° C.).

IR (mineral oil) 3351, 3198, 1684, 1612, 1600, 1578, 1536, 1503, 1495, 1316, 1283, 1271, 1232, 699, 691 cm$^{-1}$;

$^1$H NMR (300 MHz, DMSO-d$_6$) δ 13.80, 10.75, 7.00–7.35, 7.06, 6.91, 6.81, 5.01, 2.60–3.70.

EXAMPLE 51

Preparation of α-[[[(4,5-Dihydro-5-thioxo-1,3,4-thiadiazol-2-yl)amino]carbonyl]amino]-N-(3-phenylpropyl)-(S)-benzenepropanamide.

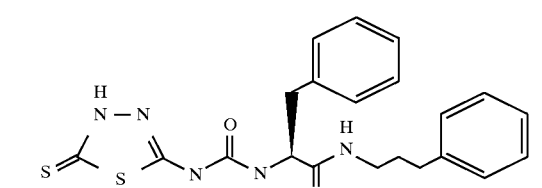

Following the general procedure outlined in EXAMPLE 5, and making non-critical variations but starting with phenpropylamine, the title compound is obtained (mp 190°–191° C.).

IR (mineral oil) 3309, 3241, 3154, 3108, 3063, 3025, 1692, 1640, 1574, 1496, 1323, 1246, 1233, 1063, 696 cm$^{-1}$;

$^1$H NMR (300 MHz, DMSO-d$_6$) δ 13.83, 10.70, 8.20–8.30, 7.10–7.30, 6.88, 4.40–4.50, 2.80–3.15, 2.40–2.55, 1.60–1.70;

MS (FAB) m/z 442, 441, 284, 283, 136, 120, 91.

EXAMPLE 52

Preparation of α-[[[(4,5-Dihydro-5-thioxo-1,3,4-thiadiazol-2-yl)amino]carbonyl]-amino]-N-[(4-trifluoromethylphenyl)methyl]-(S)-benzenepropanamide.

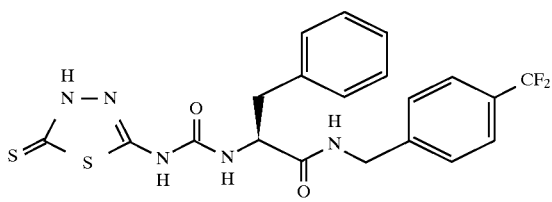

Following the general procedure outlined in EXAMPLE 5, and making non-critical variations but starting with (4-trifluoromethyl)benzylamine, the title compound is obtained (mp 217°–218° C.).

IR (mineral oil) 3323, 3193, 3131, 1690, 1644, 1582, 1568, 1549, 1494, 1326, 1228, 1162, 1122, 1113, 1067 cm$^{-1}$;

$^1$H NMR (300 MHz, DMSO-d$_6$) δ 13.82, 10.70, 8.83, 7.66, 7.15–7.40, 6.88, 4.53, 4.25–4.45, 2.80–3.10.

EXAMPLE 53

Preparation of α-[[[(4,5-Dihydro-5-thioxo-1,3,4-thiadiazol-2-yl)amino]carbonyl]amino]-N-[(4-nitrophenyl)methyl]-(S)-benzenepropanamide.

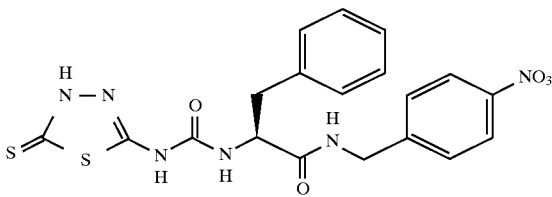

Following the general procedure outlined in EXAMPLE 5, and making non-critical variations but starting with 4-nitrobenzylamine, the title compound is obtained.

IR (mineral oil) 3275, 3103, 3082, 3026, 1697, 1646, 1607, 1573, 1544, 1520, 1496, 1345, 1319, 1232, 700 cm$^{-1}$;

$^1$H NMR (DMSO-d$_6$) δ 8.90, 8.15, 7.10–7.45, 6.93, 4.30–4.60, 2.85–3.10.

EXAMPLE 54

α-[[[(4,5-Dihydro-5-thioxo-1,3,4-thiadiazol-2-yl) amino]-carbonyl]amino]-N-[[4-(1,1-dimethylethyl)phenyl]methyl]-(S)-benzenepropanamide.

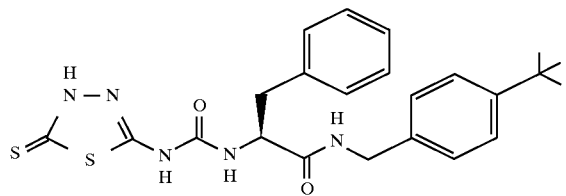

Following the general procedure outlined in EXAMPLE 5, and making non-critical variations but starting with (4-tert-butyl)benzylamine, the title compound is obtained (mp 213°–214° C.).

IR (mineral oil) 3235, 3147, 3063, 3030, 1693, 1632, 1580, 1544, 1514, 1497, 1437, 1326, 1235, 739, 698 cm$^{1}$;

$^1$H NMR (300 MHz, DMSO-d$_6$) δ 8.60–8.70, 7.05–7.35, 6.90, 4.45–4.55, 4.10–4.30, 2.80–3.10, 1.27.

EXAMPLE 55

Preparation of (S)-1-[2-[[[(4,5-Dihydro-5-thioxo-1,3,4-thiadiazol-2-yl)amino]carbonyl]amino]-1-oxo-3-phenylpropyl]-4-(benzhydryl)piperazine.

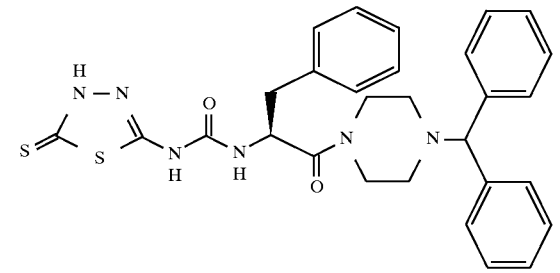

Following the general procedure outlined in EXAMPLE 5, and making non-critical variations but starting with 1-benzhydrylpiperazine, the title compound is obtained (mp 43°–44° C.).

IR (mineral oil) 3131, 3086, 3061, 3026, 1689, 1612, 1576, 1547, 1490, 1320, 1286, 1225, 1058, 704, 698 cm$^{-1}$;

$^1$H NMR (300 MHz, DMSO-d$_6$) δ 13.80, 10.70, 7.05–7.45, 6.93, 4.89, 4.24, 3.25–3.55, 2.70–2.95, 2.05–2.35, 1.85–2.00.

EXAMPLE 56

Preparation of (S)-1-[2-[[[(4,5-Dihydro-5-thioxo-1,3,4-thiadiazol-2-yl)amino]carbonyl]amino]-1-oxo-3-phenylpropyl]piperazine trifluoroacetic acid.

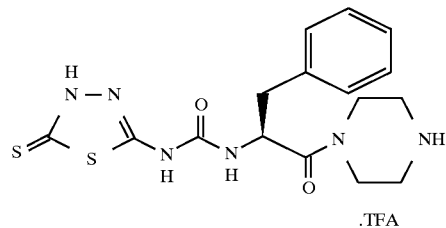

Following the general procedure outlined in EXAMPLE 5, and making non-critical variations but starting with BOC-piperazine followed by deprotection with trifluoroacetic acid, the title compound is obtained (mp 164°–166° C.).

IR (mineral oil) 3211, 3086, 3028, 1677, 1633, 1574, 1494, 1316, 1263, 1245, 1204, 1185, 1135, 724, 703 cm$^{-1}$;

$^1$H NMR (300 MHz, DMSO-d$_6$) δ 10.91, 7.15–7.35, 4.90–5.00, 3.70, 2.70–3.80;

MS (FAB) m/z 393, 392, 260, 234, 120, 87, 85.

EXAMPLE 57
Preparation of N-(1H-Benzimidazol-2-ylmethyl)-α-[[[(4,5-dihydro-5-thioxo-1,3,4-thiadiazol-2-yl)amino]carbonyl]amino]-(S)-benzenepropanamide.

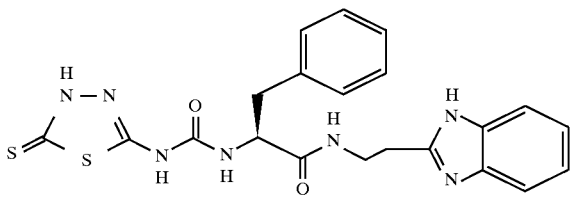

Following the general procedure outlined in EXAMPLE 5, and making non-critical variations but starting with 2-(aminomethyl)benzimidazole, the title compound is obtained.

IR (mineral oil) 3325, 3195, 1682, 1652, 1586, 1538, 1498, 1439, 1322, 1253, 1241, 1038, 744, 735, 701 cm$^{-1}$;

MS (FAB) m/z 454, 453, 321, 295, 146, 132, 131, 120.

EXAMPLE 58
Preparation of α-[[[(4,5-Dihydro-5-thioxo-1,3,4-thiadiazol-2-yl) amino]carbonyl]amino]-N-(1-naphthylmethyl)-(S)-benzenepropanamide.

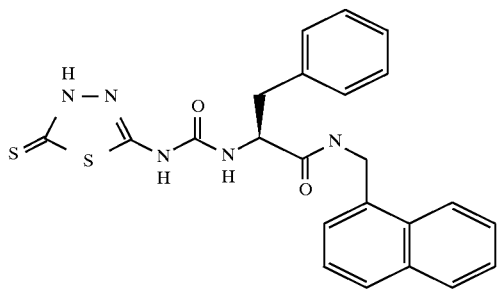

Following the general procedure outlined in EXAMPLE 5, and making non-critical variations but starting with 1-naphthalenemethylamine, the title compound is obtained (mp 234°–235° C.).

IR (mineral oil) 3300, 3087, 3062, 3028, 1693, 1640, 1574, 1548, 1512, 1496, 1321, 1236, 1063, 777, 699 cm$^{-1}$;

$^1$H NMR (300 MHz, DMSO-d$_6$) δ 8.78, 7.90–8.10, 7.86, 7.10–7.60, 6.91, 4.60–4.80, 4.50–4.60, 2.80–3.10;

MS (FAB) m/z 464, 463, 306, 305, 158, 142, 141, 120.

EXAMPLE 59
Preparation of N-[[(4,5-Dihydro-5-thioxo-1,3,4-thiadiazol-2-yl)amino]carbonyl]-L-(4-aminophenyl)alanine methyl ester.

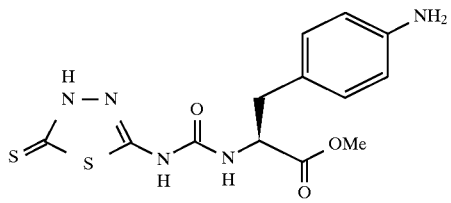

A mixture of N-[[(4,5-dihydro-5-thioxo-1,3,4-thiadiazol-2-yl)amino]carbonyl]-L-(4-aminophenyl)alanine methyl ester (EXAMPLE 33; 0.390 g, 1.02 mmol), tin (II) chloride dihydrate (1.15 g, 5.10 mmol), EtOH (5.0 mL) and EtOAc (5.0 mL) is heated at 80° C. for 2 hours. After cooling to room temperature, basic workup (EtOAc, brine wash, MgSO$_4$) gives 298 mg (83%) of the title compound.

IR (mineral oil) 3351, 3224, 3131, 1737, 1693, 1614, 1575, 1545, 1517, 1488, 1320, 1255, 1219, 1181, 1054 cm$^{-1}$;

$^1$H NMR (300 MHz, CDCl$_3$) δ 6.90, 6.65, 4.67, 3.95, 3.75, 2.90–3.10;

MS (EI) m/z 353, 147, 133, 114, 106, 76, 74, 60, 59, 57, 46.

EXAMPLE 60
Preparation of α-[[[(4,5-Dihydro-5-thioxo-1,3,4-thiadiazol-2-yl)amino]carbonyl]amino]-N-methyl-(S)-cyclohexanepropanamide.

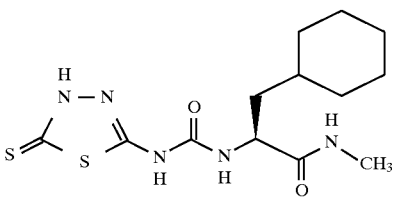

Following the general procedure outlined in EXAMPLE 5, and making non-critical variations but starting with N-[[(4,5-dihydro-5-thioxo-1,3,4-thiadiazol-2-yl)amino]carbonyl]-β-cyclohexyl-L-alanine methyl ester (prepared similarly to that described in EXAMPLE 1), the title compound is obtained (mp 246°–247° C.).

[α]$^{25}_D$+13° (c 0.98, DMSO);

IR (mineral oil) 3317, 3266, 3143, 3106, 3011, 1688, 1646, 1573, 1492, 1323, 1287, 1253, 1233, 1061, 687 cm$^{-1}$;

$^1$H NMR (300 MHz, DMSO-d$_6$) δ 13.60–14.10, 10.30–10.80, 8.11, 6.82, 4.00–4.25, 2.58, 0.60–1.85;

MS (EI) m/z 343, 211, 159, 133, 127, 126, 86, 83, 69, 58, 55.

EXAMPLE 61
Preparation α-[[[(4,5-Dihydro-5-thioxo-1,3,4-thiadiazol-2-yl)amino]carbonyl]amino]-N-(phenylmethyl)-(S)-cyclohexanepropanamide.

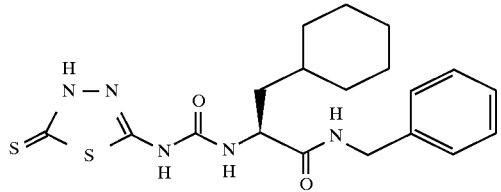

Following the general procedure outlined in EXAMPLE 5, and making non-critical variations but starting with N-[[(4,5-dihydro-5-thioxo-1,3,4-thiadiazol-2-yl)amino]carbonyl]-p-cyclohexyl-L-alanine methyl ester (prepared similarly to that described in EXAMPLE 1) and benzylamine, the title compound is obtained (mp 198°–199° C.).

[α]$^{25}_D$–22° (c 0.99, DMSO);

IR (mineral oil) 3219, 3179, 3130, 3088, 3031, 1691, 1633, 1581, 1536, 1496, 1438, 1331, 1325, 1233, 699 cm$^{-1}$;

$^1$H NMR (300 MHz, DMSO-d$_6$) δ 13.50–14 10, 10.40–10.90, 8.60–8.85, 7.10–7.45, 6.86, 4.05–4.45, 0.75–1.90;

MS (FAB) m/z 420, 496, 421, 420, 287, 262, 261, 126, 108, 106, 91.

EXAMPLE 62

Preparation of α-[[[(4,5-Dihydro-5-thioxo-1,3,4-thiadiazol-2-yl)amino]carbonyl]amino]-N-(2-phenylethyl)-(S)-cyclohexanepropanamide.

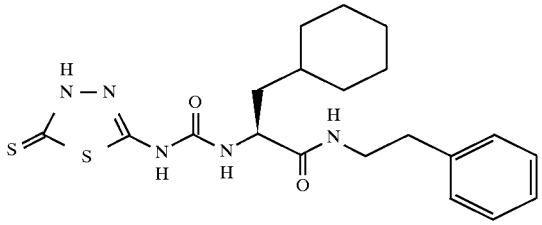

Following the general procedure outlined in EXAMPLE 5, and making non-critical variations but starting with N-[[(4,5-dihydro-5-thioxo-1,3,4-thiadiazol-2-yl)amino]carbonyl]-β-cyclohexyl-L-alanine methyl ester (prepared similarly to that described in EXAMPLE 1) and phenethylamine, the title compound is obtained (mp 199°–200° C.).

$[\alpha]^{25}_D$ -25° (c 0.97, DMSO);

IR (mineral oil) 3243, 3156, 3116, 3026, 1695, 1642, 1575, 1496, 1321, 1280, 1235, 1060, 742, 698, 685 cm$^{-1}$;

$^1$H NMR (300 MHz, DMSO-d$_6$) δ 13.84, 10W60, 8.15–8.35, 7.10–7.40, 6.70–6.90, 4.10–4.35, 3.15–3.50, 2.71, 0.70–1.90;

MS (FAB) m/z 434, 433, 301, 276, 275, 126, 122, 105.

EXAMPLE 63

Preparation of N-[[(4,5-Dihydro-5-thioxo-1,3,4-thiadiazol-2-yl)amino]carbonyl]-O-(phenylmethyl)-L-serine methyl ester.

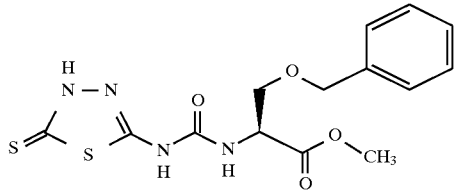

Following the general procedure outlined in EXAMPLE 1, and making non-critical variations but starting with O-(phenylmethyl)-L-serine methyl ester hydrochloride, the title compound is obtained (mp 84°–86° C.).

$[\alpha]^{25}_D$ (MeOH)=+12°;

IR (mineral oil) 3210, 3089, 3066, 3029, 1746, 1699, 1577, 1544, 1495, 1344, 1319, 1214, 1106, 1073, 1059 cm$^{-1}$;

$^1$H NMR (DMSO) δ 3.63–3.70, 3.68, 3.84, 4.48, 4.55, 4.54–4.56, 7.13, 7.28–7.39, 10.85, 13.87.

EXAMPLE 64

Preparation of N-[[(4,5-Dihydro-5-thioxo-1,3,4-thiadiazol-2-yl)amino]carbonyl]-O-(phenylmethyl)-L-threonine methyl ester.

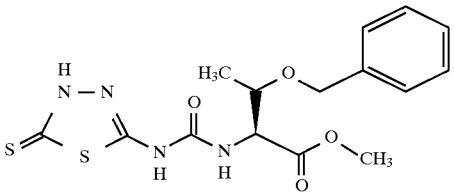

Following the general procedure outlined in EXAMPLE 1, and making non-critical variations but starting with O-(phenylmethyl)-L-threonine methyl ester hydrochloride, the title compound is obtained (mp 88°–90° C.).

$[\alpha]^{25}_D$ (MeOH)=−17°;

IR (mineral oil) 3227, 3127, 3089, 3028, 1962, 1748, 1700, 1576, 1544, 1496, 1483, 1318, 1213, 1089, 1059 cm$^{-1}$;

$^1$H NMR (DMSO) δ 1.19, 3.63, 4.11, 4.36, 4.41, 4.58, 7.01, 7.26–7.39, 10.76, 13.79.

EXAMPLE 65

Preparation of N-[[(4,5-Dihydro-5-thioxo-1,3,4-thiadiazol-2-yl)amino]carbonyl]-S-[(4-methylphenyl)methyl]-L-cysteine methyl ester

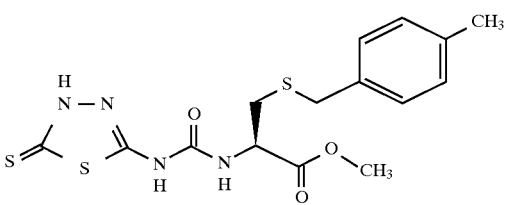

Following the general procedure outlined in EXAMPLE 1, and making non-critical variations but starting with S-[(4-methylphenyl)methyl]-L-cysteine methyl ester hydrochloride, the title compound is obtained (mp 124°–125° C.).

$[\alpha]^{25}_D$ (MeOH)=+15°;

IR (mineral oil) 3396, 3295, 3046, 1911, 1723, 1681, 1581, 1539, 1513, 1492, 1444, 1323, 1240, 1215, 1057 cm$^{-1}$;

$^1$H NMR (DMSO) δ 2.34, 2.84–2.88, 3.67, 3.71, 4.53–4.60, 7.10–7.19, 10.94, 13.88;

MS (FAB) m/z 399, 398, 240, 1056

EXAMPLE 66

Preparation of 2-[[[(4,5-Dihydro-5-thioxo-1,3,4-thiadiazol-2-yl)amino]carbonyl]-amino]-N-methyl-3-(phenylmethoxy)-(2S)-butanamide.

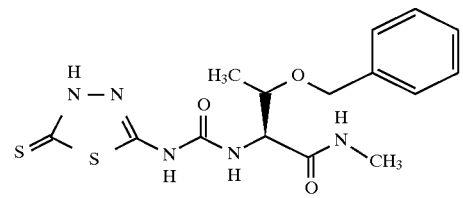

Following the general procedure outlined in EXAMPLE 5, and making non-critical variations but starting with N-[[(4,5-Dihydro-5-thioxo-1,3,4-thiadiazol-2-yl)amino]carbonyl]-O-(phenylmethyl)-L-threonine methyl ester (EXAMPLE 64), the title compound is obtained (mp 187°–189° C. decomposition).

$[\alpha]^{25}_D$ (MeOH)=+6°;

IR (mineral oil) 3321, 3122, 3027, 1996, 1695, 1644, 1575, 1546, 1495, 1320, 1241, 1227, 1091, 1056, 698 cm$^{-1}$;

$^1$H NMR (DMSO) δ 1.12, 2.62, 4.01, 4.16, 4.40, 4.54, 6.90, 7.27–7.33, 8.03, 10.81, 13.85;

MS (FAB) m/z 382, 381, 224, 223, 133, 91.

EXAMPLE 67

Preparation of N-[[(4,5-Dihydro-5-thioxo-1,3,4-thiadiazol-2-yl)amino]carbonyl]-O-(1,1-dimethylethoxy)-L-serine methyl ester.

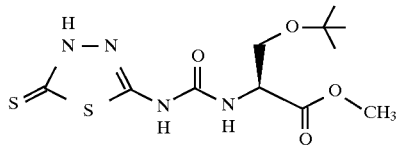

Following the general procedure outlined in EXAMPLE 1, and making non-critical variations but starting with O-(tert-butyl)-L-serine methyl ester hydrochloride, the title compound is obtained.

IR (mineral oil) 3223, 2350, 2141, 1747, 1700, 1578, 1541, 1393, 1347, 1319, 1234, 1214, 1100, 1072, 1057 cm$^{-1}$;

$^1$H NMR (DMSO) δ 1.09, 3.51, 3.65, 3.72, 4.45, 6.90, 10.82, 13.85.

EXAMPLE 68

Preparation of N-[[(4,5-Dihydro-5-thioxo-1,3,4-thiadiazol-2-yl)amino]carbonyl]-S-[(4-methoxyphenyl)methyl]-L-cysteine methyl ester.

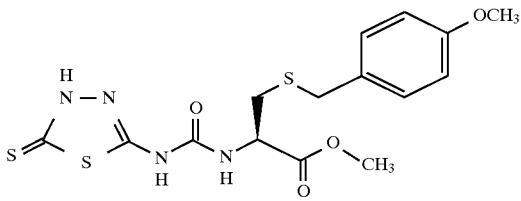

Following the general procedure outlined in EXAMPLE 1, and making non-critical variations but starting with S-[(4-methoxyphenyl)methyl]-L-cysteine methyl ester hydrochloride, the title compound is obtained.

$[α]^{25}_D$ (MeOH)=+15°;

IR (mineral oil) 3399, 3314, 3242, 1722, 1681, 1611, 1582, 1538, 1512, 1487, 322, 1233, 1217, 1055, 618 cm$^{-1}$;

$^1$H NMR (DMSO) δ 2.84, 3.67, 3.70, 3.72, 4.56, 6.86, 7.14, 7.20, 10.95, 13.89.

EXAMPLE 69

Preparation of 2-[[[(4,5-Dihydro-5-thioxo-1,3,4-thiadiazol-2-yl)amino]carbonyl]amino]-N-methyl-3-phenylmethoxy-(S)-propanamide.

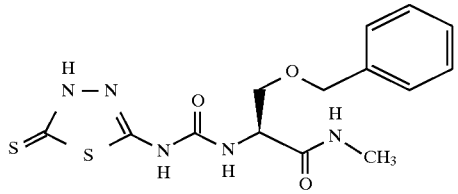

Following the general procedure outlined in EXAMPLE 5, and making non-critical variations but starting with N-[[(4,5-dihydro-5-thioxo-1,3,4-thiadiazol-2-yl)amino]carbonyl]-O-(phenylmethyl)-L-serine methyl ester (EXAMPLE 63), the title compound is obtained (195°–196° C. decomposition).

$[α]^{25}_D$ (MeOH)=+19°;

IR (mineral oil) 3328, 3087, 3058, 3030, 1709, 1642, 1576, 1545, 1495, 1415, 1322, 1234, 1218, 1058, 698 cm$^{-1}$;

$^1$H NMR (DMSO) δ 2.61, 3.57, 3.70, 4.32–4.37, 4.48, 7.01, 7.26–7.37, 8.11, 10.84, 13.85.

EXAMPLE 70

Preparation of 2-[[[(4,5-Dihydro-5-thioxo-1,3,4-thiadiazol-2-yl)amino]-carbonyl]amino]-N-methyl-3-[[(4-methylphenyl) methyl]thio]-(R)-propanamide.

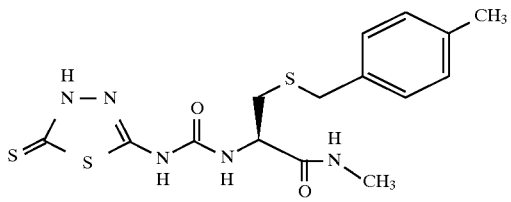

Following the general procedure outlined in EXAMPLE 5, and making non-critical variations but starting with N-[[(4,5-Dihydro-5-thioxo-1,3,4-thiadiazol-2-yl)amino]carbonyl]-S-[(4-methylphenyl)methyl]-L-cysteine methyl ester (EXAMPLE 65), the title compound is obtained (209°–211° C. decomposition).

$[α]^{25}_D$ (DMSO)=+68°;

IR (mineral oil) 3329, 3226, 3181, 3124, 3025, 1914, 1695, 1688, 1640, 1592, 1582, 1546, 1513, 1411, 1232 cm$^{-1}$;

$^1$H NMR (DMSO) δ 2.08, 2.44, 2.48–2.52, 3.51, 4.21, 6.83, 6.92, 7.00, 8.05, 10.58, 13.66.

EXAMPLE 71

Preparation of N-[[(4,5-Dihydro-5-thioxo-1,3,4-thiadiazol-2-yl)amino]carbonyl]-S-(phenylmethyl)-L-cysteine methyl ester.

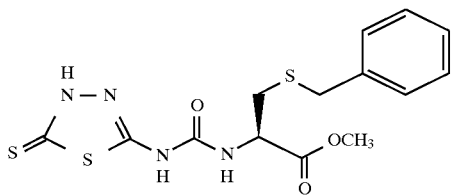

Following the general procedure outlined in EXAMPLE 1, and making non-critical variations but starting with S-(phenylmethyl)-L-cysteine methyl ester hydrochloride, the title compound is obtained (mp 169°–172° C.).

$[α]^{25}_D$ [α(MeOH)=+8°;

IR (mineral oil) 3380, 2345, 2170, 1996, 1959, 1940, 1712, 1684, 1578, 1550, 1545, 1481, 1306, 1291, 1243 cm$^{-1}$;

1H NMR (DMSO) δ 2.97–3.00, 3.80, 3.89, 4.70, 7.30, 7.38–7.45, 11.08, 14.01.

EXAMPLE 72

Preparation of 2-[[[(4,5-Dihydro-5-thioxo-1,3,4-thiadiazol-2-yl)amino]carbonyl]-amino]-N-methyl-3-[(phenylmethyl)thio]-(R)-propanamide.

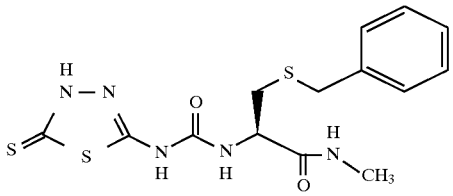

Following the general procedure outlined in EXAMPLE 5, and making non-critical variations but starting with N-[[(4,5-dihydro-5-thioxo-1,3,4-thiadiazol-2-yl)amino]carbonyl]-S-(phenylmethyl)-L-cysteine methyl ester (EXAMPLE 71), the title compound is obtained (197°–199° C. decomposition).

[α]$^{25}_D$ (MeOH)=+47°;

IR (mineral oil) 3311, 3198, 3084, 3027, 1706, 1690, 1639, 1575, 1544, 1494, 1415, 1321, 1230, 1054, 698 cm$^{-1}$;

$^1$H NMR (DMSO) δ 2.56, 2.59, 2.68, 3.67, 4.34, 6.96, 7.16–7.24, 8.18, 10.69, 13.73.

EXAMPLE 73

Preparation of 2-[[[(4,5-Dihydro-5-thioxo-1,3,4-thiadiazol-2-yl)amino]carbonyl]-amino]-3-(1,1-dimethylethoxy)-N-methyl-(S)-propanamide.

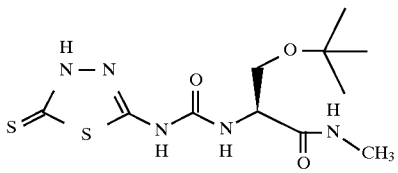

Following the general procedure outlined in EXAMPLE 5, and making non-critical variations but starting with O-(tert-butyl)-N-[[(4,5-dihydro-5-thioxo-1,3,4-thiadiazol-2-yl)amino]carbonyl]-L-serine methyl ester (EXAMPLE 69), the title compound is obtained.

IR (mineral oil) 3278, 3177, 2173, 1693, 1640, 1583, 1547, 1528, 1490, 1322, 1253, 1233, 1222, 1196, 1071 cm$^{-1}$;

$^1$H NMR (DMSO) δ 1.07, 2.58, 3.42, 3.55, 4.15, 6.78, 10.85, 13.82.

EXAMPLE 74

Preparation of N-[[(4,5-Dihydro-5-thioxo-1,3,4-thiadiazol-2-yl)amino]carbonyl]-O-(1,1-dimethylethoxy)-L-threonine methyl ester.

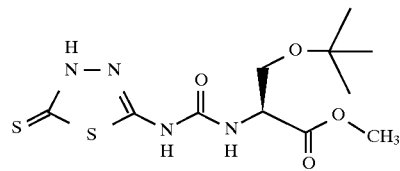

Following the general procedure outlined in EXAMPLE 1, and making non-critical variations but starting with O-(tert-butyl)-L-threonine methyl ester hydrochloride, the title compound is obtained.

IR (mineral oil) 3221, 2157, 1751, 1701, 1675, 1576, 1540, 1346, 1312, 1270, 1257, 1209, 1159, 1085, 1059 cm$^{-1}$;

1H NMR (DMSO) δ 1.08, 1.12, 3.65, 4.23, 6.83, 10.96, 13.87.

EXAMPLE 75

Preparation of 2-[[[(4,5-Dihydro-5-thioxo-1,3,4-thiadiazol-2-yl)amino]-carbonyl]amino]-3-(1,1-dimethylethoxy)-N-methyl-(S)-butanamide.

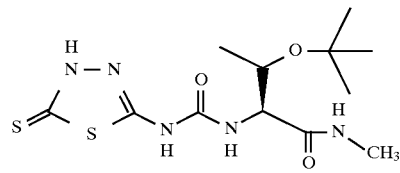

Following the general procedure outlined in EXAMPLE 5, and making non-critical variations but starting with N-[[(4,5-dihydro-5-thioxo-1,3,4-thiadiazol-2-yl)amino]carbonyl]-O-(1,1-dimethylethoxy)-L-threonine methyl ester (EXAMPLE 74), the title compound is obtained.

IR (mineral oil) 3339, 3184, 1996, 1701, 1645, 1576, 1535, 1494, 1412, 1314, 1268, 1218, 1193, 1082, 1059 cm$^{-1}$;

$^1$H NMR (DMSO) δ 1.01, 1.07, 2.57, 3.99, 6.85, 7.81, 10.9, 13.8.

EXAMPLE 76

Preparation of α-[[[(4,5-Dihydro-5-thioxo-1,3,4-thiadiazol-2-yl)-amino]carbonyl]amino]-N-[5-[[[5-(dimethylamino)-1-naphthaleny 1] sulfonyl]amino]pentyl]-(S)-benzenepropanamide.

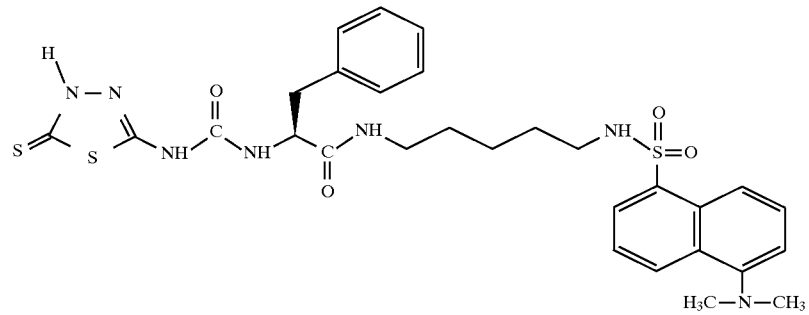

The product of EXAMPLE 1 (91 mg), monodansylcadaverine (251 mg), methanol (1.0 mL), and tetrahydrofuran (3.0 mL) are stirred together at room temperature for 4 days. The reaction mixture is evaporated to dryness, redissolved in dichloromethane and subjected to flash chromatography on silica gel eluting first with 5% methanol in dichloromethane. Fractions containing product are evaporated to dryness, triturated with dichloromethane and filtered. The resulting solid is retriturated in dichloromethane containing some hexane and filtered to yield the title compound as a yellow solid.

$^1$HNMR (300 MHz, d$_6$ DMSO) 0.9–1.35, 2.65–3.0, 4.3–4.45, 5.76 (CH$_2$Cl$_2$), 6.8–6.85, 7.05–7.3, 7.55–7.7, 7.8, 8.0–8,15, 8.3–8.35, 8.4–8.5, 10.65, 13.8;

MS (FAB) m/z: 642, 719, 644, 643, 642, 484, 336, 171, 170, 169, 120.

EXAMPLE 77

Preparation of α-[[[(4,5-Dihydro-5-thioxo-1,3,4-thiadiazol-2-yl)amino]carbonyl]amino]-N-methyl-(2,3,4,5,6-pentafluorobenzene)-(S)-benzene-propanamide.

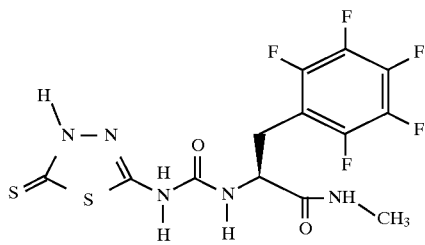

Following the general procedures outlined in EXAMPLE 1 and then EXAMPLE 5, and making non-critical variations but starting with L-2-amino-3-(2,3,4,5,6-pentafluorophenyl)-propionic acid methyl ester, the title compound is obtained.

IR (mull) 3199, 3124, 3087, 1696, 1641, 1591, 1568, 1555, 1519, 1504, 1412, 1236, 1126, 981, 967;

$^1$HNMR (300 MHz, d$_6$ DMSO) δ 2.56–2.57, 2.9–3.2, 4.4–4.5, 6.9–7.0, 8.2–8.3, 10.6, 13.8;

MS (EI) m/z: 427, 396, 269, 210, 181, 163, 159, 133, 87, 58.

EXAMPLE 78

Preparation of α-[[[(4,5-Dihydro-5-thioxo-1,3,4-thiadiazol-2-yl) amino]carbonyl]amino]-(S)-(1,1'-biphenyl)-4-propanoic acid methyl ester.

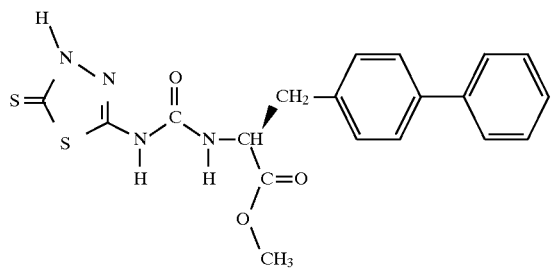

Following the general procedure outlined in EXAMPLE 1, and making non-critical variations but starting with L-2-amino-3-(4-biphenyl)-propionic acid methyl ester, the title compound is obtained.

$^1$HNMR (300 MHz, d$_6$ DMSO) δ 3.09–3.18, 3.71, 4.61–4.63, 6.97–7.0, 7.27–7.67, 10.86, 13.86;

MS (FAB) m/z: 415, 523, 493, 492, 491, 416, 415, 414, 256, 167, 134.

EXAMPLE 79

Preparation of α-[[[(4,5-Dihydro-5-thioxo-1,3,4-thiadiazol-2-yl) amino]carbonyl]amino]-N-methyl-(S)-(1,1'-biphenyl)-4-propanamide.

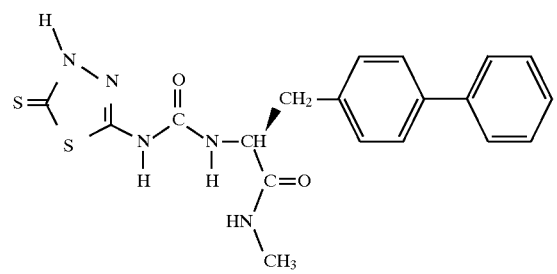

Following the general procedures outlined in EXAMPLE 5, and making non-critical variations but starting with the product of EXAMPLE 78 (0.20 g, the title compound is obtained as a white solid.

$^1$HNMR (300 MHz, d$_6$ DMSO) δ 2.58–2.60, 2.8–2.95, 2.98–3.1, 4.4–4.5, 6.9, 7.2–7.7, 8.05–8.15;

(FAB) M/S: 414, 491, 490, 415, 414, 413, 256, 255, 196, 167, 32;

EXAMPLE 80

Preparation of N-[[[(4,5-Dihydro-5-thioxo-1,3,4-thiadiazol-2-yl) amino]carbonyl]-4-(1,1-dimethylethyl)-L-phenylalanine methyl ester.

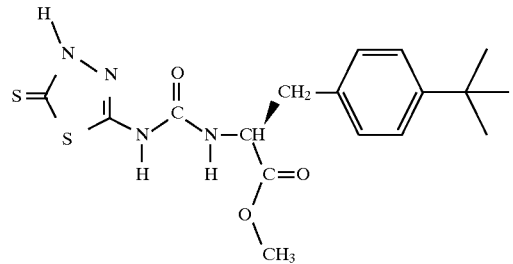

Following the general procedure outlined in EXAMPLE 1, and making non-critical variations but starting with L-2-amino-3-(4-tert-butyl-phenyl)-propionic acid methyl ester the title compound is obtained.

$^1$HNMR (300 MHz, d$_6$ DMSO) δ 1.20–1.26, 2.94–3.07, 3.68, 4.53–4.55, 6.89–6.92, 7.07–7.10, 7.31–7.34;

MS (EI) m/z: 394, 176, 159, 148, 147, 133, 132, 117, 88, 66, 57;

EXAMPLE 81

Preparation of α-[[[(4,5-dihydro-5-thioxo-1,3,4-thiadiazol-2-yl) amino]carbonyl]amino]-4-(1,1-dimethylethyl)-N-methyl-(S)-benzenepropanamide.

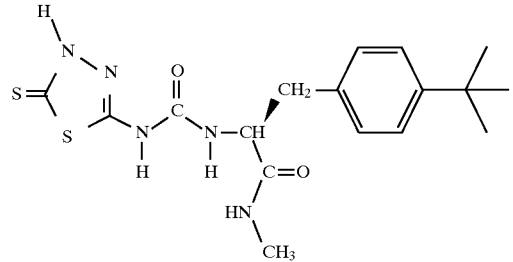

Following the general procedure of EXAMPLE 5 and making non-critical variations but starting with the product of EXAMPLE 80, the title compound is obtained.

$^1$HNMR (300 MHz, d$_6$ DMSO) δ 1.25, 2.55–2.65, 2.7–2.85, 2.90–3.0, 4.3–4.4, 6.8, 7.05–7.15, 7.25–7.35, 8.1;

MS (EI) m/z: 393, 217, 202, 176, 159, 147, 133, 120, 87, 69, 57;

EXAMPLE 82

Preparation of N-[[(4,5-Dihydro-5-thioxo-1,3,4-thiadiazol-2-yl) amino]thioxomethyl]-L-phenylalanine methyl ester.

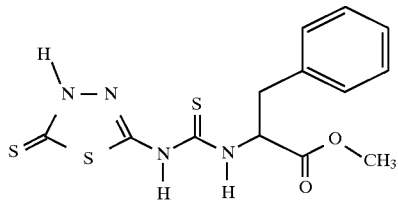

5-Amino-1,3,4-thiadiazole-2-thiol, 0.74 g (5.3 mmol) and L-2-isothiocyanato-3-phenyl propionic acid methyl ester, 1.0 g (5.3 mmol) is added to DMF and stirring under $N_2$ initiated. DABCO (1,4-diazabicyclo[2.2.2.]octane), 0.57 g (5.3 mmol) is added and the mixture is stirred for 25 hours. It is transferred to an ice/10% HCl mixture and extracted with 3×250 ml of $CHCl_3$:$CH_{30}H$ (9:1). The extract is evaporated and the concentrate added to diethyl ether and filtered. The filtrate is concentrated and added to hexane. The hexane mixture is filtered to yield the title compound.

MS (FAB) m/z: 355, 431, 399, 372, 355, 323, 322 321, 296, 120, 85;

MS (EI) m/z : 354, 322, 175, 133, 128, 120, 103, 91, 87, 76, 70;

$^1$H NMR (DMSO) δ 8.25, 6.97–7.15, 4.83, 3.45, 2.87–3.05.

EXAMPLE 83

Preparation of α-[[[(4,5-Dihydro-5-thioxo-1,3,4-thiadiazol-2-yl) amino]thioxomethyl]amino]-N-methyl-(S)-benzenepropanamide.

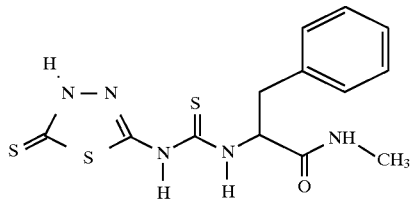

Following the general procedure of EXAMPLE 5, and making non-critical variations but starting with the product of EXAMPLE 82, the title compound is obtained.

IR (mineral oil) 3259, 3114, 3066, 1951, 1656, 1578, 1534, 1495, 1358, 1320, 1282, 1220, 1062, 738, 699 cm$^{-1}$;

$^1$H NMR (DMSO) δ 8.49, 8.17, 7.08–7.26, 4.82–4.90, 2.89–3.12, 2.53–2.56;

MS (FAB) m/z: 354, 431, 430, 399, 354, 323, 295, 179, 162, 133, 120;

MS (EI) m/z: 353, 322, 175, 162, 133, 128, 120, 103, 91, 87, 74.

EXAMPLE 84

Preparation of P-[[[(4,5-Dihydro-5-thioxo-1,3,4-thiadiazol-2-yl) amino]carbonyl]amino]-benzenebutanoic acid ethyl ester.

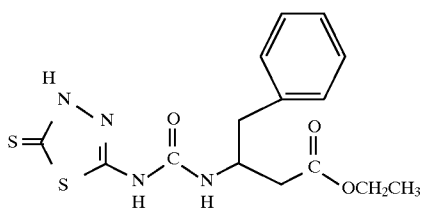

A solution of 3-amino-4-phenyl-butyric acid ethyl ester (0.606 g, 2.92 mmol) and diisopropylethylamine (0.6 mL; 3 mmol) in 25 mL $CH_2Cl_2$ is added dropwise over 30 minutes to a solution of triphosgene (0.329 g, 1.11 mmol) in 25 mL dry THF under $N_2$. The solution is stirred an additional 30 minutes, then 5-amino-1,3,4-thiadiazole-2-thiol (0.390 g, 2.92 mmol) and diisopropylethylamine (0.6 mL, 3 mmol) are added and the reaction is allowed to stir at room temperature overnight. The reaction is concentrated, the residue taken up in 50 mL $CH_2Cl_2$, washed with 25 mL 10% aq. KHSO4 and 25 mL brine, and dried ($Na_2SO_4$) The organic phase is absorbed onto silica gel and chromatographed with 3% MeOH/$CH_2Cl_2$. A pale yellow solid is obtained, which is dissolved in MeOH/$CH_2Cl_2$ and concentrated to a slurry in vacuo. The resulting title compound is obtained as white solid (mp 192°–193° C.).

IR (mineral oil) 3356, 3208, 3083, 3032, 1721, 1676, 1575, 1554, 1493, 1321, 1262, 1255, 1210, 1045, 688 cm$^{-1}$;

$^1$H NMR (DMSO) δ 1.16, 2.43–2.57, 2.81, 4.04, 4.16–4.24, 6.68, 7.18–7.24, 7.31–7.34, 10.72, 13.81;

MS (EI) m/z: 366, 190, 159, 133, 120, 117, 116, 91, 83, 74, 70.

EXAMPLE 85

Preparation of β-[[[(4,5-Dihydro-5-thioxo-1,3,4-thiadiazol-2-yl) amino]carbonyl]amino]methyl-N-methylbenzenebutanamide.

The product of EXAMPLE 86 (0.352 g, 0.960 mmol) and 10 mL EtOH saturated with gaseous methylamine are stirred at ambient temperature overnight. The reaction is absorbed onto silica gel and chromatographed with 5% MeOH/$CH_2Cl_2$ to afford 0.164 g (0.466 mmol; 48%) product as a white solid (233°–234° C. decomposition).

IR (mineral oil) 3336, 1705, 1684, 1622, 1581, 1558, 1495, 1413, 1330, 1297, 1248, 1057, 1028, 738, 699 cm$^{-1}$;

$^1$H NMR (DMSO) δ 2.11–2.25, 2.47, 2.67, 3.98–4.10, 6.67, 7.05–7.12, 7.16–7.21, 7.77, 10.64, 13.67;

MS (FAB) m/z: 352, 504, 460, 429, 428, 352, 351, 219, 193, 177, 101.

EXAMPLE 86

Preparation of α-[[[(4,5-Dihydro-5-thioxo-1,3,4-thiadiazol-2-yl)-amino]carbonyl]amino]methyl]-N-methylbenzenepropanamide.

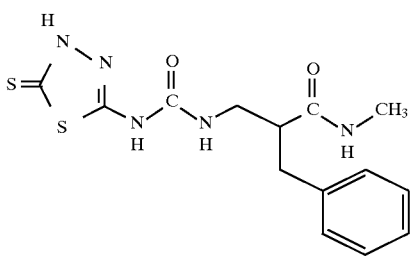

Step 1. Preparation of α-[[[[(4,5-Dihydro-5-thioxo-1,3,4-thiadiazol-2-yl)-amino]carbonyl]amino]methyl]benzene propanoic acid, methyl ester.

A solution of 2-aminomethyl-3-phenyl-propionic acid methyl ester (1.04 g, 3.46 mmol) and diisopropylethylamine (1.8 mL, 7.61 mmol) in 25 mL $CH_2Cl_2$ is added dropwise over 50 minutes to a solution of triphosgene (0.385 g, 1.30 mmol) in 30 mL dry THF under $N_2$. The solution is stirred an additional 30 minutes, then 5-amino-1,3,4-thiadiazole-2-thiol (0.466 g, 3.50 mmol) and diisopropylethylamine (0.6 mL, 4 mmol) are added and the reaction is allowed to stir at room temperature overnight. The reaction is concentrated, the residue taken up in 50 mL $CH_2Cl_2$, washed with 25 mL 10% aq. KHSO4 and 25 mL brine, and dried ($Na_2SO_4$). The organic phase is absorbed onto silica gel and chromatographed with 2% $MeOH/CH_2Cl_2$. A pale yellow foam is obtained, which upon recrystallization from $CH_2Cl_2$/hexane afforded 0.141 g (0.40 mmol; 12%) as a white solid.

IR (mull) 3139, 3086, 3026, 1734, 1703, 16900 1676, 1576, 1548, 1533, 1496, 1328, 1234, 1066, 700 $cm^{-1}$;

$^1$H NMR (DMSO) δ 2.81–2.93, 3.33–3.35, 3.580 6.81, 7.15–7.35, 10.85, 13.86;

MS (EI) m/z: 352, 159, 133, 131, 117, 104, 102, 91, 83, 78, 70.

Step 2. Preparation of α-[[[[(4,5-Dihydro-5-thioxo-1,3,4-thiadiazol-2-yl)-amino]carbonyl]amino]methyl]-N-methylbenzenepropanamide The product of EXAMPLE 86, step 1 (0.330 g, 0.937 mmol) and 10 mL EtOH saturated with gaseous methylamine are stirred at ambient temperature overnight. The reaction is absorbed onto silica gel and chromatographed with 5% $MeOH/CH_2Cl_2$. The product that precipitated out of the fractions is collected to afford the title compound 0.072 g (0.20 mmol; 22%) product as a white solid (214°–6° C. decomposition).

$^1$H NMR (DMSO) δ 2.53, 2.52–2.70, 2.75–2.85, 3.13–3.27, 6.66, 7.14–7.22, 7.28–7.30, 7.90, 10.61, 13.81;

IR (mineral oil) 3349, 3177, 3084, 3025, 1685, 1633, 1585, 1542, 1495, 1409, 1319, 1280, 1246, 1055, 697 $cm^{-1}$;

EXAMPLE 87

Preparation of N-(4,5-Dihydro-5-thioxo-1,3,4-thiadiazol-2-yl)-N'-2-phenylethyl-urea.

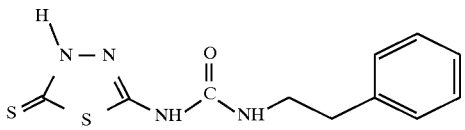

5-Amino-1,3,4-thiadiazole-2-thiol (2.00 g, 0.015 mol) is allowed to react overnight with phenethyl isocyanate (2.1 g, 0.015 mol) in dry THF (50 mL) under an inert atmosphere at room temperature. The THF is removed under reduced pressure to give the crude product as a solid. The crude product is dissolved in acetone and diluted with water and loaded onto a preparative C-18 reverse-phase column. The column is developed with an acetone/water gradient. The fractions are monitored by reverse-phase TLC using 70% acetone/30% water as the eluent and visualizing the plates with short-wave UV Fractions containing pure product are combined and evaporated to yield a white solid after drying under vacuum. (2.68 g, 67%).

$^1$H NMR (DMSO) δ 2.75, 3.35, 6.60, 7.19–7.34, 10.78, 13.79;

MS (EI): m/z: 280, 133, 105, 91, 77, 65.

EXAMPLE 88

Preparation of N-(4,5-Dihydro-5-thioxo-1,3,4-thiadiazol-2-yl)-N'-phenylmethyl-urea.

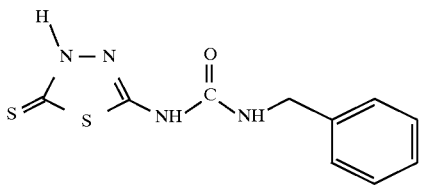

Following the general procedure of EXAMPLE 87 and making non-critical variations but starting with benzyl isocyanate, the title compound is obtained.

IR (Mineral Oil): 2953, 2926, 2871, 2856, 1705, 1698, 1573, 1488 $cm^{-1}$;

$^1$H NMR (DMSO) δ: 13.68, 10.84, 7.30–7.13, 7.03, 4.20;

MS (EI): m/z: 266, 159, 133, 107, 106, 91, 83, 79, 78, 77, 76.

SCHEME I

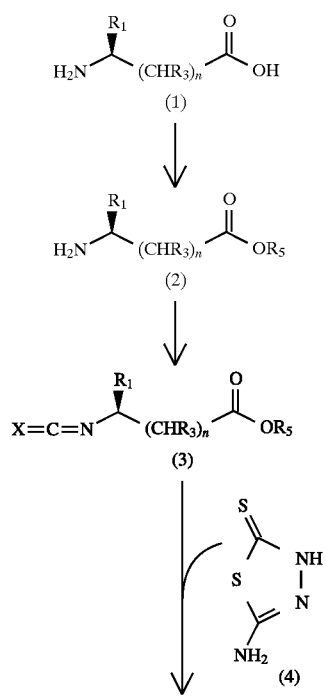

-continued
SCHEME I

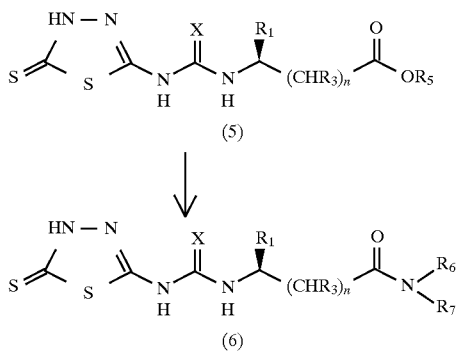

SCHEME II

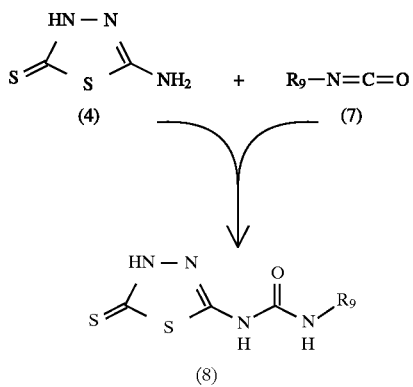

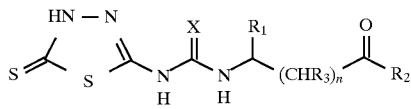

We claim:
1. A compound of formula I

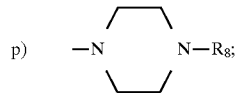

or pharmaceutical acceptable salts thereof wherein:
x is
  a) O, or
  b) S;
$R_1$ is
  a) H,
  b) $C_{1-6}$ alkyl,
  c) —$(CH_2)_i$-aryl,
  d) —$(CH_2)_j$-cycloalkyl,
  e) —$(C_{1-4}$ alkyl)—O—$R_4$,
  f) —$(C_{1-4}$ alkyl)—S—$R_4$,
  f) —$(CH_2)_j$-Het,
  g) —C(=O)—O—$R_4$,
  h) —C(=O)—$NR_5R_5$, or
  i) —$(CH_2)$—O—$Si(R_4)_3$;
$R_2$ is
  a) —O—$R_5$, or
  b) —$NR_6R_7$;
$R_3$ is
  a) H,
  b) $C_{1-6}$ alkyl,
  c) —$(CH_2)_i$-aryl,
  d) —$(CH_2)_j$-cycloalkyl,
  e) —$(C_{1-4}$ alkyl)—O—$R_4$,
  f) —$(C_{1-4}$ alkyl)—S—$R_4$, or
  g) —$OR_4$;
$R_4$ is
  a) H,
  b) $C_{1-6}$ alkyl, or
  c) —$(CH_2)_i$-aryl;
$R_5$ is
  a) H,
  b) $C_{1-6}$ alkyl, or
  c) aryl;
$R_6$ and $R_7$ may be the same or differently
  a) H,
  b) $C_{1-6}$ alkyl,
  c) $C_{1-6}$ $OR_4$,
  d) —$(CH_2)_i$-aryl,
  e) —$(CH_2)_j$-cycloalkyl,
  f) —$(CH_2)_j$-Het,
  g) —$(CH_2)$—Q,
  h) —$(CH_2)$—C(=O)—$OR_4$,
  i) —$(CH_2)_j$—C(=O)—$NR_5R_5$,
  j) 5-(((5-(dimethylamino)-1-naphthalenyl)sulfonyl) amino)pentyl, or
$R_6$ and $R_7$ taken together with the linking N-atom to form
  k) azetidinyl,
  l) pyrrolidinyl,
  m) piperidinyl,
  n) morpholino,
  o) 4-thiomorpholinyl, or p) —N⟨ ⟩N—$R_8$;

$R_8$ is
  a) H,
  b) $C_{1-6}$ alkyl,
  c) —$(CH_2)_i$-aryl,
  d) benzhydryl, or
  e) —$(CH_2)_i$-Het;
aryl is
  phenyl, biphenyl, or naphthalene, optionally substituted with one to five of the following:
  a) $C_{1-4}$ alkyl,
  b) —$OR_4$,
  c) halogen,
  d) —$NR_5R_5$,
  e) —C(=O)—$NR_5R_5$,
  f) —NHC(=O)$R_4$,
  g) —$SO_2NR_5R_5$,
  h) —$NHSO_2R_5$,
  i) —$NO_2$,
  j) —$CF_3$, or
  k) —O—$Si(R_4)_3$;
Het is
  a 5-, 6-, 9-, or 10-membered heteroaromatic moiety having one or more atoms selected from the group consisting of N, O, and S;
Q is
  a saturated 5-, or 6-membered heterocyclic moiety having 1–2 atoms selected from the group consisting of N, O, and S;
i is 0, 1, 2, 3, or 4;
j is 1, 2, 3, or 4;
n is 0, or 1;

with the following provisos:
a) where $R_1$ is isobutyl, $R_6$ and $R_7$ are other than methyl,
b) where $R_1$ is isobutyl, $R_5$ is other than methyl.
c) where X is O at least one of $R_1$ and $R_3$ is other than H, or $C_{1-6}$ alkyl
d) where $R_1$ and $R_3$ is $C_{1-6}$ alkyl, $R_5$ is other than H or $C_{1-6}$ alkyl, and
e) where $R_1$ and $R_3$ is $C_{1-6}$ alkyl, at least one of $R_6$ and $R_7$ is other than H or $C_{16}$ alkyl.

2. A compound of formula I according to claim I which is an optically pure enantiomer having structure II

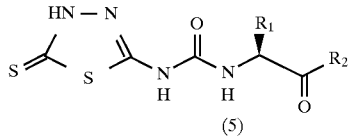

wherein $R_1$ and $R_2$ are the same as defined in claim 1.

3. A compound of claim 1 wherein $R_1$ is phenyl, benzyl, 4-tert-butyphenylmethyl, 4-bromophenylmethyl, 4-fluorophenylmethyl, 4-methoxyphenylmethyl, 4-nitrophenylmethyl, 4-hydroxyphenylmethyl, 4-aminophenylmethyl, 2,3,4,5,6,-pentafluorophenylmethyl, cyclohexylmethyl, benzyloxymethyl, 1-benzyloxyethyl, 2-indolylmethyl, benzylthiomethyl, 4-methylbenzylthiomethyl, 4-methyloxybenzylthiomethyl, tert-butyloxymethyl, 1-tert-butyloxyethyl, biphenylmethyl, or isobutyl.

4. A compound of claim 1 wherein $R_6$ and $R_7$ are hydrogen, methyl, isopropyl, n-butyl, cyclohexylmethyl, 3-hydroxypropyl, benzyl, 3,4-dimethoxyphenylmethyl, 2-phenylethyl, 4-trifluoromethyphenylmethyl, 4-nitrophenylmethyl, 4-tertbutylphenylmethyl, 3-phenylpropyl, 4-phenylbutyl, 2-pyridylmethyl, 3-pyridylmethyl, 4-pyridyl methyl, 2-benzimidazolemethyl, 1-naphthylmethyl, 2-morpholinoethyl, or piperonylmethyl, N-methyl-,β-alaninamide, or β-alanine.

5. A compound of claim 1 wherein $R_6$ and $R_7$ taken together with the linking N-atom are morpholino, pyrrolidinyl, piperidinyl, 4-thiomorpholinyl, 4-phenylpiperazinyl, 4-benzylpiperazinyl, 4-(4-methoxyphenyl)piperazinyl, 4-(2-pyrimidinyl)piperazinyl, 4-(2-pyridyl)piperazinyl, or 4-benzhydryl.

6. A compound of claim 1 wherein said compound of formula I is (1) N-[[(4,5-Dihydro-5-thioxo-1,3,4-thiadiazol-2-yl)amino]carbonyl]-L-phenylalanine methyl ester,
(2) α-[[[(4,5-Dihydro-5-thioxo-1,3,4-thiadiazol-2-yl)amino]carbonyl]amino]-N-methyl-(S)-benzenepropanamide,
(3) N-[[(4,5-Dihydro-5-thioxo-1,3,4-thiadiazol-2-yl)amino]carbonyl]-D-phenylalanine methyl ester,
(4) α-[[[(4,5-Dihydro-5-thioxo-1,3,4-thiadiazol-2-yl)amino]carbonyl]amino]-N-methyl-(R)-benzenepropanamide,
(5) α-[[[(4,5-Dihydro-5-thioxo-1,3,4-thiadiazol-2-yl)amino]carbonyl]amino]-N-(phenylmethyl)-(S)-benzenepropanamide,
(6) α-[[[(4,5-Dihydro-5-thioxo-1,3,4-thiadiazol-2-yl)amino]carbonyl]amino]-N-(phenylethyl)-(S)-benzenepropanamide,
(7) α-[[[(4,5-Dihydro-5-thioxo-1,3,4-thiadiazol-2-yl)amino]carbonyl]amino]-N-(2-pyridinylmethyl)-(S)-benzenepropanamide,
(8) α-[[[(4,5-Dihydro-5-thioxo-1,3,4-thiadiazol-2-yl)amino]carbonyl]amino]-N,N-dimethyl-(S)-benzenepropanamide,
(9) α-[[[(4,5-Dihydro-5-thioxo-1,3,4-thiadiazol-2-yl)amino]carbonyl]amino]-(S)-benzenepropanamide,
(10) α-[[[(4,5-Dihydro-5-thioxo-1,3,4-thiadiazol-2-yl)amino]carbonyl]amino]-N-(1-methylethyl)-(S)-benzenepropanamide,
(11) N-Butyl-α-[[[(4,5-dihydro-5-thioxo-1,3,4-thiadiazol-2-yl)amino]carbonyl]amino]-(S)-benzenepropanamide,
(12) N-[[(4,5-Dihydro-5-thioxo-1,3,4-thiadiazol-2-yl)amino]carbonyl]-L-phenylalanine,
(13) α-[[[(4,5-Dihydro-5-thioxo-1,3,4-thiadiazol-2-yl)amino]carbonyl]amino]-N-methyl-(S)-1H-indole-3-propanamide,
(14) (S)-1-[2-[[[(4,5-Dihydro-5-thioxo-1,3,4-thiadiazol-2-yl)amino]carbonyl]amino]-1-oxo-3-phenylpropyl]-4-(phenylmethyl)piperazine,
(15) (S)-1-[2-[[[(4,5-Dihydro-5-thioxo-1,3,4-thiadiazol-2-yl)amino]carbonyl]amino]-1-oxo-3-phenylpropyl]-4-(2-pyridinyl)piperazine,
(16) α-[[[(4,5-Dihydro-5-thioxo-1,3,4-thiadiazol-2-yl)amino]carbonyl]amino]-N-[(3,4-dimethoxyphenyl)methyl]-(S)-benzenepropanamide,
(17) α-[[[(4,5-Dihydro-5-thioxo-1,3,4-thiadiazol-2-yl)amino]carbonyl]amino]-N-(4-pyridinylmethyl)-(S)-benzenepropanamide,
(18) α-[[[(4,5-Dihydro-5-thioxo-1,3,4-thiadiazol-2-yl)amino]carbonyl]amino]-N-(3-pyridinylmethyl)-(S)-benzenepropanamide,
(19) α-[[[(4,5-Dihydro-5-thioxo-1,3,4-thiadiazol-2-yl)amino]carbonyl]amino]-N-[2-(4-morpholinyl)ethyl]-(S)-benzenepropanamide,
(20) α-[[[(4,5-Dihydro-5-thioxo-1,3,4-thiadiazol-2-yl)amino]carbonyl]amino]-N-methyl-4-bromobenzenepropanamide,
(21) (S)-1-[2-[[[(4,5-Dihydro-5-thioxo-1,3,4-thiadiazol-2-yl)amino]carbonyl]amino]-1-oxo-3-phenylpropyl]-4-(4-methoxyphenyl)piperazine,
(22) (S)-1-[2-[[[(4,5-Dihydro-5-thioxo-1,3,4-thiadiazol-2-yl)amino]carbonyl]amino]-1-oxo-3-phenylpropyl]-4-(2-pyrimidinyl)piperazine,
(23) (S)-1-[2-[[[(4,5-Dihydro-5-thioxo-1,3,4-thiadiazol-2-yl)amino]carbonyl]amino]-1-oxo-3-(pentafluorophenyl)propyl]-4-(2-pyridinyl)piperazine,
(24) (S)-N-[[(4,5-Dihydro-5-thioxo-1,3,4-thiadiazol-2-yl)amino]carbonyl]-2-phenylglycine methyl ester,
(25) α-[[[(4,5-Dihydro-5-thioxo-1,3,4-thiadiazol-2-yl)amino]carbonyl]amino]-N-methyl-(S)-benzeneacetamide,
(26) α-[[[(4,5-Dihydro-5-thioxo-1,3,4-thiadiazol-2-yl)amino]carbonyl]amino]-4-fluoro-N-methyl-(S)-benzenepropanamide,
(27) (S)-1-[2-[[[(4,5-Dihydro-5-thioxo-1,3,4-thiadiazol-2-yl)amino]carbonyl]amino]-1-oxo-3-(4-fluorophenyl)propyl]-4-(2-pyridinyl)piperazine,
(30) N-[[(4,5-Dihydro-5-thioxo-1,3,4-thiadiazol-2-yl)amino]carbonyl]-O-methyl-L-tyrosine methyl ester,
(31) α-[[[(4,5-Dihydro-5-thioxo-1,3,4-thiadiazol-2-yl)amino]carbonyl]amino]-4-methoxy-N-methyl-(S)-benzenepropanamide,
(32) N-[[(4,5-Dihydro-5-thioxo-1,3,4-thiadiazol-2-yl)amino]carbonyl]-L-(4-nitrophenyl)alanine methyl ester,
(33) α-[[[(4,5-Dihydro-5-thioxo-1,3,4-thiadiazol-2-yl)amino]carbonyl]amino]-N-methyl-4-nitro-(S)-benzenepropanamide,
(34) α-[[[(4,5-Dihydro-5-thioxo-1,3,4-thiadiazol-2-yl)amino]carbonyl]amino]-4-nitro-N-(2-phenylethyl)-(S)-benzenepropanamide,
(35) N-Butyl-α-[[[(4,5-dihydro-5-thioxo-1,3,4-thiadiazol-2-yl)amino]carbonyl]amino]-4-nitro-(S)-benzenepropanamide,

(36) (S)-4-[2-[[[(4,5-Dihydro-5-thioxo-1,3,4-thiadiazol-2-yl)amino]carbonyl]amino]-1-oxo-3-phenylpropyl] morpholine,
(37) α-[[[(4,5-Dihydro-5-thioxo-1,3,4-thiadiazol-2-yl)amino]carbonyl]amino]-N-(4-phenylbutyl)-(S)-benzenepropanamide,
(38) N-Cyclohexylmethyl-α-[[[(4,5-Dihydro-5-thioxo-1,3,4-thiadiazol-2-yl)amino]carbonyl]amino]-(S)-benzenepropanamide,
(39) (S)-4-[2-[[[(4,5-Dihydro-5-thioxo-1,3,4-thiadiazol-2-yl)amino]carbonyl]amino]-1-oxo-3-phenylpropyl] pyrrolidine,
(40) (S)-4-[2-[[[(4,5-Dihydro-5-thioxo-1,3,4-thiadiazol-2-yl)amino]carbonyl]amino]-1-oxo-3-phenylpropyl] thiomorpholine,
(41) α-[[[(4,5-Dihydro-5-thioxo-1,3,4-thiadiazol-2-yl)amino]carbonyl]amino]-N-(3-hydroxypropyl)-(S)-benzenepropanamide,
(42) N-[[[(4,5-Dihydro-5-thioxo-1,3,4-thiadiazol-2-yl)amino]carbonyl]-L-phenylalanyl-β-alanine ethyl ester,
(43) N-[[(4,5-Dihydro-5-thioxo-1,3,4-thiadiazol-2-yl)amino]carbonyl]-L-phenylalanyl-N-methyl-β-alaninamide,
(44) N-[[[(4,5-Dihydro-5-thioxo-1,3,4-thiadiazol-2-yl)amino]carbonyl]-L-phenylalanyl-β-alanine,
(45) N-[[(4,5-Dihydro-5-thioxo-1,3,4-thiadiazol-2-yl)amino]carbonyl]-O-[(1,1-dimethylethyl)dimethylsilyl]-L-serine methyl ester,
(46) 2-[[[(4,5-Dihydro-5-thioxo-1,3,4-thiadiazol-2-yl)amino]carbonyl]amino]-3-[(1,1-dimethylethyl)dimethylsilyloxyl-N-methyl-(S)-propanamide,
(47) N-[[(4,5-Dihydro-5-thioxo-1,3,4-thiadiazol-2-yl)amino]carbonyl]-O-[(1,1-dimethylethyl)dimethylsilyl]-L-tyrosine methyl ester,
(48) α-[[[(4,5-Dihydro-5-thioxo-1,3,4-thiadiazol-2-yl)amino]carbonyl]amino]-4-hydroxy-N-methyl-(S)-benzenepropanamide,
(49) α-[[[(4,5-Dihydro-5-thioxo-1,3,4-thiadiazol-2-yl)amino]carbonyl]amino]-N-(piperonyl)-(S)-benzenepropanamide,
(50) (S)-1-[2-[[[(4,5-Dihydro-5-thioxo-1,3,4-thiadiazol-2-yl)amino]carbonyl]amino]-1-oxo-3-phenylpropyl]-4-phenylpiperazine,
(51) α-[[[(4,5-Dihydro-5-thioxo-1,3,4-thiadiazol-2-yl)amino]carbonyl]amino]-N-(3-phenylpropyl)-(S)-benzenepropanamide,
(52) α-[[[(4,5-Dihydro-5-thioxo-1,3,4-thiadiazol-2-yl)amino]carbonyl]amino]-N-[(4-trifluoromethylphenyl)methyl]-(S)-benzenepropanamide,
(53) α-[[[(4,5-Dihydro-5-thioxo-1,3,4-thiadiazol-2-yl)amino]carbonyl]amino]-N-[(4-nitrophenyl)methyl]-(S)-benzenepropanamide,
(54) x-[[[(4,5-Dihydro-5-thioxo-1,3,4-thiadiazol-2-yl)amino]carbonyl]amino]-N-[[4-(1,1-dimethylethyl)phenyl]methyl]-(S)-benzenepropanamide,
(55) (S)-1-[2-[[[(4,5-Dihydro-5-thioxo-1,3,4-thiadiazol-2-yl)amino]carbonyl]amino]-1-oxo-3-phenylpropyl]-4-(benzhydryl)piperazine,
(56) (S)-1-[2-[[[(4,5-Dihydro-5-thioxo-1,3,4-thiadiazol-2-yl)amino]carbonyl]amino]-1-oxo-3-phenylpropyl] piperazine trifluoroacetic acid,
(57) N-(1H-Benzimidazol-2-ylmethyl)-α-[[[(4,5-dihydro-5-thioxo-1,3,4-thiadiazol-2-yl)amino]carbonyl]amino]-(S)-benzenepropanamnide,
(58) α-[[[(4,5-Dihydro-5-thioxo-1,3,4-thiadiazol-2-yl)amino]carbonyl]amino]-N-(1-naphthylmethyl)-(S)-benzenepropanamide,
(59) N-[[(4,5-Dihydro-5-thioxo-1,3,4-thiadiazol-2-yl)amino]carbonyl]-L-(4-aminophenyl)alanine methyl ester,
(60) α-[[[(4,5-Dihydro-5-thioxo-1,3,4-thiadiazol-2-yleamino]carbonyl]amino]-N-methyl-(S)-cyclohexanepropanamide,
(61) α-[[[(4,5-Dihydro-5-thioxo-1,3,4-thiadiazol-2-yl)amino]carbonyl]amino]-N-(phenylmethyl)-(S)-cyclohexanepropanamide,
(62) α-[[[(4,5-Dihydro-5-thioxo-1,3,4-thiadiazol-2-yl)amino]carbonyl]amino]-N-(2-phenylethyl)-(S)-cyclohexanepropanamide,
(63) N-[[(4,5-Dihydro-5-thioxo-1,3,4-thiadiazol-2-yl)amino]carbonyl]-O-(phenylmethyl)-L-serine methyl ester,
(64) N-[[(4,5-Dihydro-5-thioxo-1,3,4-thiadiazol-2-yl)amino]carbonyl]-O-(phenylmethyl)-L-threonine methyl ester,
(65) N-[[(4,5-Dihydro-5-thioxo-1,3,4-thiadiazol-2-yl)amino]carbonyl]-S-[(4-methylphenyl)methyl]-L-cysteine methyl ester,
(66) 2-[[[(4,5-Dihydro-5-thioxo-1,3,4-thiadiazol-2-yl)amino]carbonyl]amino]-N-methyl-3-(phenylmethoxy)-(2S)-butanamide,
(67) N-[[(4,5-Dihydro-5-thioxo-1,3,4-thiadiazol-2-yl)amino]carbonyl]-O-(1,1-dimethylethoxy)-L-serine methyl ester,
(68) N-[[(4,5-Dihydro-S-thioxo-1,3,4-thiadiazol-2-yl)amino]carbonyl]-S-[(4-methoxyphenyl)methyl]-L-cysteine methyl ester,
(69) 2-[[[(4,5-Dihydro-5-thioxo-1,3,4-thiadiazol-2-yl)amino]carbonyl]amino]-N-methyl-3-phenylmethoxy-(S)-propanamide,
(70) 2-[[[(4,5-Dihydro-5-thioxo-1,3,4-thiadiazol-2-yl)amino]carbonyl]amino]-N-methyl-3-[[(4-methylphenyl)methyl]thio]-(R)-propanamide,
(71) N-[[(4,5-Dihydro-5-thioxo-1,3,4-thiadiazol-2-yl)amino]carbonyl]-S-(phenylmethyl)-L-cysteine methyl ester,
(72) 2-[[[(4,5-Dihydro-5-thioxo-1,3,4-thiadiazol-2-yl)amino]carbonyl]amino]-N-methyl-3-[(phenylmethyl)thio]-(R)-propanamide,
(73) 2-[[[(4,5-Dihydro-5-thioxo-1,3,4-thiadiazol-2-yl)amino]carbonyl]amino]-3-(1,1-dimethylethoxy)-N-methyl-(S)-propanamide,
(74) N-[[(4,5-Dihydro-5-thioxo-1,3,4-thiadiazol-2-yl)amino]carbonyl]-O-(1,1-dimethylethoxy)-L-threonine methyl ester,
(75) 2-[[[(4,5-Dihydro-5-thioxo-1,3,4-thiadiazol-2-yl)amino]carbonyl]amino]-3-(1,1-dimethylethoxy)-N-methyl-(S)-butanamide,
(76) α-[[[(4,5-Dihydro-5-thioxo-1,3,4-thiadiazol-2-yl)-amino]carbonyl]amino]-N-[5-[[[5-(dimethylamino)-1-naphthalenyl] sulfonyl]amino]pentyl]-(S)-benzenepropanarnide,
(77) α-[[[(4,5-Dihydro-5-thioxo-1,3,4-thiadiazol-2-yl)amino]carbonyl]amino]-N-methyl-(2,3,4,5,6-pentafluorobenzene)-(S)-benzene-propanamide,
(78) α-[[[(4,5-Dihydro-5-thioxo-1,3,4-thiadiazol-2-yl)amino]carbonyl]amino]-(S)-(1,1'-biphenyl)-4-propanoic acid methyl ester,
(79) α-[[[(4,5-Dihydro-5-thioxo-1,3,4-thiadiazol-2-yl)amino]carbonyl]amino]-N-methyl-(S)-(1,1'-biphenyl)-4-propanamide,
(80) N-[[(4,5-Dihydro-5-thioxo-1,3,4-thiadiazol-2-yl)amino]carbonyl]-4-(1,1-dimethylethyl)-L-phenylalanine methyl ester,
(81) α-[[[(4,5-dihydro-5-thioxo-1,3,4-thiadiazol-2-yl)amino]carbonyl]amino]-4-(1,1-dimethylethyl)-N-methyl-(S)-benzenepropanamide,

(82) N-[[(4,5-Dihydro-5-thioxo-1,3,4-thiadiazol-2-yl)amino]thioxomethyl]-L-phenylalanine methyl ester,

(83) α-[[[(4,5-Dihydro-5-thioxo-1,3,4-thiadiazol-2-yl)amino]thioxomethyl]amino]-N-methyl-(S)-benzenepropanamide,

(84) β-[[[(4,5-Dihydro-5-thioxo-1,3,4-thiadiazol-2-yl)amino]carbonyl]amino]-benzenebutanoic acid ethyl ester,

(85) D-[[[[(4,5-Dihydro-5-thioxo-1,3,4-thiadiazol-2-yl)amino]carbonyl]amino]methyl]-N-methylbenzenepropanamide, or

(86) α-[[[[(4,5-Dihydro-5-thioxo-1,3,4-thiadiazol-2-yl)amino]carbonyl]amino]methyl]-N-methylbenzenepropanamide.

7. A compound of claim 6 which is (S)-1-[2-[[[(4,5-Dihydro-5-thioxo-1,3,4-thiadiazol-2-yl)amino]carbonyl]amino]-1-oxo-3-(pentafluorophenyl)propyl]-4-(2-pyridinyl)piperazine, or α-[[[(4,5-Dihydro-5-thioxo-1,3,4-thiadiazol-2-yl)amino]carbonyl]amino]-N-methyl-(2,3,4,5,6-pentafluorobenzene)-(S)-benzene-propanamide.

8. A method of inhibiting excess matrix metalloproteinase which comprises administering to a patient in need thereof an effective amount of a compound of claim 1.

9. A method of claim 8 wherein matrix metalloproteinases comprises stromelysin.

10. A method of treating a human, suffering from or susceptible to a diseases involving connective tissue degradation which comprises administering to a patient in need thereof an effective amount of a compound of claim 1.

11. A method of claim 10 wherein the diseases related to connective tissue degradation is osteoarthrits, rheumatoid arthritis, septic arthritis, osteopenias such as osteoporosis, tumor metastasis (invasion and growth), periodontitis, gingivitis, corneal ulceration, dermal ulceration, or gastric ulceration.

12. A pharmaceutical composition which comprises an amount of the compound of claim 1 effective to inhibit excess matrix metalloproteinase and a pharmaceutically acceptable carrier.

13. The method of claim 8 wherein the effective amount of the compound of claim 1 is administered orally, parenterally, or topically in a pharmaceutical composition.

14. The method of claim 10 wherein the effective amount of the compound of claim 1 is administered orally, parenterally, or topically in a pharmaceutical composition.

15. The method of claim 8 or 10 wherein said compound is administered in an amount of from about 0.1 to about 100 mg/kg of body weight/day.

\* \* \* \* \*